US009242985B2

United States Patent
Kühne et al.

(10) Patent No.: US 9,242,985 B2
(45) Date of Patent: Jan. 26, 2016

(54) STRUCTURAL MIMETICS OF PROLINE-RICH PEPTIDES AND USE THEREOF

(75) Inventors: Ronald Kühne, Berlin (DE); Hartmut Oschkinat, Berlin (DE); Robert Opitz, Berlin (DE); Matthias Müller, Berlin (DE); Hans-Günther Schmalz, Brühl (DE); Cedric Reuter, Köln (DE); Peter Huy, Korschenbroich (DE)

(73) Assignees: FORSCHUNGSVERBUND BERLIN E.V., Berlin (DE); UNIVERSITÄT ZU KÖLN, Köln (DE)

( * ) Notice: Subject to any disclaimer, the term of this patent is extended or adjusted under 35 U.S.C. 154(b) by 0 days.

(21) Appl. No.: 14/241,245

(22) PCT Filed: Aug. 24, 2012

(86) PCT No.: PCT/EP2012/066506
§ 371 (c)(1),
(2), (4) Date: Mar. 28, 2014

(87) PCT Pub. No.: WO2013/030111
PCT Pub. Date: Mar. 7, 2013

(65) Prior Publication Data
US 2015/0018269 A1    Jan. 15, 2015

(30) Foreign Application Priority Data

Aug. 26, 2011  (EP) .................................. 11179040

(51) Int. Cl.
| *A01N 37/18*  | (2006.01) |
| *A61K 38/04*  | (2006.01) |
| *C07D 471/20* | (2006.01) |
| *A61K 31/437* | (2006.01) |
| *C07K 5/078*  | (2006.01) |
| *C07K 7/06*   | (2006.01) |
| *A61K 38/00*  | (2006.01) |

(52) U.S. Cl.
CPC ............ *C07D 471/20* (2013.01); *A61K 31/437* (2013.01); *C07K 5/06139* (2013.01); *C07K 7/06* (2013.01); *A61K 38/00* (2013.01)

(58) Field of Classification Search
CPC ........ A61K 38/00; A61K 38/04; A01N 37/46
See application file for complete search history.

(56) References Cited

FOREIGN PATENT DOCUMENTS

| WO | WO 98/54208 A1    | 12/1998 |
| WO | WO 2006/067091 A1 | 6/2006  |
| WO | WO 2008/040332 A1 | 4/2008  |
| WO | WO 2011/003626 A1 | 1/2011  |

OTHER PUBLICATIONS

Freund, C. et al. 2008 "Proline-rich sequence recognition domains (PRD): Ligands, function and inhibition" in *Protein-Protein Interactions as New Drug Targets*, Springer-Verlag, Berlin Heidelberg pp. 407-430.
Vartak, A.P. et al. 2006 "Concerted synthesis of a spirobicyclic Type-VI β-Turn mimic of Pro-Pro-Pro-$NH_2$" Organic Letters 8: 983-986.
Witter, D.J. et al. 1998 "Design and synthesis of SH3 domain binding ligands: modifications of the consensus sequence XPpXP" *Bioorganic & Medicinal Chemistry Letters* 8: 3137-3142.
Zaminer, J. et al. 2010 "Addressing protein-protein interactions with small molecules: a Pro-pro dipeptide mimic with a PPII helix conformation as a module for the synthesis of PRD-binding ligands" *Angewandte Chemie. International Edition* 49: 7111-7115.
Zimmermann, J. et al. "Design of N-substituted peptomer ligands for EVH1 Domains" *Journal of Biological Chemistry* 278: 36810-36818, 2003.

*Primary Examiner* — Marcela M Cordero Garcia
*Assistant Examiner* — Kaipeen Yang
(74) *Attorney, Agent, or Firm* — Knobbe, Martens, Olson & Bear, LLP

(57) ABSTRACT

The invention relates to compounds that can be used, in particular, as structural mimetics of proline-rich peptides and are correspondingly able to bond with proline-rich-motif binding domains (PRM domains) of proteins. The invention further relates to the use of these compounds as pharmaceutically active agents, as well as the use of the pharmaceutically active agents for the treatment of bacterial, neurodegenerative and tumor diseases.

15 Claims, 5 Drawing Sheets

A

Crystal structure of the diproline motif in PPII conformation
Crystal structure of 85
Crystal structure of X

B

Crystal structure of the diproline motif in PPII conformation
Crystal structure or 85
Crystal structure of X

SEQUENCE LISTING

```
<160> NUMBER OF SEQ ID NOS: 8

<210> SEQ ID NO 1
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 1

Pro Xaa Xaa Pro Xaa Xaa Pro
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 2

Pro Pro Xaa Pro Pro Xaa Pro Pro Xaa
1               5

<210> SEQ ID NO 3
<211> LENGTH: 13
<212> TYPE: PRT
<213> ORGANISM: Artificial Sequence
<220> FEATURE:
<223> OTHER INFORMATION: synthetic peptide
```

```
-continued

<400> SEQUENCE: 3

Ser Phe Glu Phe Pro Pro Pro Thr Glu Asp Glu Leu
1               5                   10

<210> SEQ ID NO 4
<211> LENGTH: 5
<212> TYPE: PRT
<213> ORGANISM: Artificial Sequence
<220> FEATURE:
<223> OTHER INFORMATION: synthetic peptide

<400> SEQUENCE: 4

Phe Pro Pro Pro Pro
1               5

<210> SEQ ID NO 5
<211> LENGTH: 6
<212> TYPE: PRT
<213> ORGANISM: Artificial Sequence
<220> FEATURE:
<223> OTHER INFORMATION: synthetic peptide

<400> SEQUENCE: 5

Phe Pro Pro Pro Pro Thr
1               5

<210> SEQ ID NO 6
<211> LENGTH: 3
<212> TYPE: PRT
<213> ORGANISM: Artificial Sequence
<220> FEATURE:
<223> OTHER INFORMATION: synthetic peptide

<400> SEQUENCE: 6

Ser Phe Glu
1

<210> SEQ ID NO 7
<211> LENGTH: 5
<212> TYPE: PRT
<213> ORGANISM: Artificial Sequence
<220> FEATURE:
<223> OTHER INFORMATION: synthetic peptide

<400> SEQUENCE: 7

Thr Glu Asp Glu Leu
1               5

<210> SEQ ID NO 8
<211> LENGTH: 9
<212> TYPE: PRT
<213> ORGANISM: Artificial Sequence
<220> FEATURE:
<223> OTHER INFORMATION: synthetic peptide

<400> SEQUENCE: 8

Pro Pro Pro Pro Thr Glu Asp Glu Leu
1               5
```

STRUCTURAL MIMETICS OF PROLINE-RICH PEPTIDES AND USE THEREOF

FIELD OF THE INVENTION

The invention relates to compounds that can be used, in particular, as structural mimetics of proline-rich peptides and that are therefore able to bind to proline-rich-motif binding domains (PRM binding domains) of proteins; the invention further relates to the use of these compounds as pharmaceutically active agents, as well as the use of these pharmaceutically active agents in the treatment of bacterial diseases as well as neurodegenerative and tumor diseases.

REFERENCE TO SEQUENCE LISTING

The present application is filed along with a Sequence Listing in electronic format. The Sequence Listing is provided as a file entitled 18983413 1.TXT, created Sep. 26, 2014, which is approximately 2.34 KB in size. The information in the electronic format of the Sequence Listing is incorporated herein by reference in its entirety.

BACKGROUND OF THE INVENTION

Peptides and proteins are essential components of organisms and have a variety of different functions. While proteins mainly have biocatalytical tasks (enzymes), as well as other related tasks they must perform in their capacity as important tissue components, peptides have important functions inside the organism, primarily as hormones, neurotransmitters and neuromodulators. By binding to membrane-bonded receptors, and the subsequent reactions in the cell physiology that are thereby mediated, peptides influence the communication from one cell to another cell and control a variety of vital processes, such as metabolism, immune response, digestion, respiration, pain sensation, reproduction, behavior, electrolyte balance, and more.

There exists therefore a need in the prior art to understand the precise relationships inside the organism, while providing, simultaneously, a necessary foundation for devising therapies in the treatment of pathogenic conditions. With the evolving discovery of the workings of biological processes on the molecular level, the interdisciplinary integration of biology and chemistry has evolved, supported by great advances in analytical processes and computer-supported theoretical methods. All of the above are important requirements for any successful identification of leads in the development of new active agents. Nevertheless, the road to the actual goal, which is the simple and efficient novel design of active agents, is still long-winding and remote. Typically, when working from natural structures as a starting point, comprehensive empirical research is required to synthesize libraries of possible target substances and optimize these agents for a certain activity. Moreover, aside from the high time requirement and cost expenditure, it is often found at a later time down the road that computer-developed active substances frequently exhibit the desired efficacy only inadequately in real and very complex biological systems (for example, in humans), or they have unacceptable side effects.

With this background in mind, the development, particularly also of peptidic and/or peptidemimetic active agents, is a great challenge, also in terms of the tasks that are involved in synthesizing them; in fact, in the context of the varied interdisciplinary interaction, it is ultimately the discipline of organic synthesis chemistry that determines what is feasible in terms of the possibilities and limitations for gaining access to the desired target molecules. Since, typically, these molecules must be constructed in as few steps as possible while still exhibiting stereoselectivity, new and better synthesis methodologies are always needed to meet this goal not only in the laboratory but down the road also in the context of large-scale applications. Structural mimetics of diproline units and the use thereof as a substituent in proline-riche peptides with PPII helix conformations are part of the prior art.

Some beta-turn peptide mimetics are known in the art as modulators of protein-protein interactions. WO 2006/067091 A1 discloses different peptides and peptide mimetics that prevent the homodimerization of MyD88 as well as the interaction between MyD88 and TIR. Beta-turn peptide mimetics are also known as modulators of protein-protein interactions between SH3 domains. For example, WO 98/54208 discloses that beta-turn peptide mimetics that include polyproline motifs and an alpha-helix structure are able to interact with SH3 domains. Witter et al (Bioorg. & Med. Chem. Let. 8 (1998) 3137) and Vartak et al (Organic Let. 2006, 8:5, 983) disclose different beta-turn peptide mimetics that can be used as mimetics for a polyproline sequence.

Known peptide mimetics, however, have a saturated central six-membered ring. Contrary to the prior art, the compounds according to the invention are characterized by an unsaturated central six-membered ring. The double bond in the central six-membered ring according to formula 1 of the present invention represents a considerable improvement in contrast to the prior art, due to increased stability of the compound and surprisingly improved affinity relative to target structures. All other known structures are of such a type so as to provide for the presence of a central 7-ring system that is connected to a side ring by two adjacent ring C atoms (WO 2008/040332 A1). The main advantage of the new scaffold lies in the fact that, due to the modified position of the vinylidene bridge, different steric demands emerge during the bonding step, contributing to considerable gains in terms of affinity, for example relative to EVH1 domains or, however, relative to other structures.

SUMMARY OF THE INVENTION

Therefore, it was the object of the present invention to provide compounds that can be used as mimetics for proline-rich peptides, particularly when the same have a PPII helix conformation. The proline-proline dipeptide units, particularly those with a PPII helix conformation, can preferably function as ligands for so-called PRM binding domains (PRM=proline-rich motifs).

Surprisingly, the problem according to the invention is solved by providing a compound of the general formula 1,

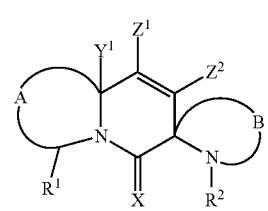

with an unsaturated central six-membered ring, wherein
X=O or S;
A, B=ring bridges;
$Y^1$=H, alkyl, fluoroalkyl, aryl or heteroaryl;

$Z^1$, $Z^2$=H; carbonyl; OH; O-alkyl; O-acyl; N—R'R" (with R' and R"=H, alkyl, acyl, sulfonyl); alkyl; acyl; fluoralkyl; aryl or heteroaryl;

$R^1$=alkyl, acyl, alkoxycarbonyl, aryloxycarbonyl, aminocarbonyl or CONH-peptidyl;

$R^2$=H, alkyl, aryl, alkylcarbonyl, arylcarbonyl, alkoxycarbonyl, aminocarbonyl, aryloxycarbonyl, alkylsulfonyl, arylsulfonyl, aminoacyl or peptidyl.

It came as a complete surprise that the compounds according to the invention do not have the disadvantages of the prior art. Aside from the aforementioned disadvantages associated with the prior art, to date the use of peptidic active agents as drug products has also been limited by a number of further factors:

1) Low metabolic stability due to proteolysis in the gastrointestinal tract and in serum;
2) Low ability to enter cells;
3) Poor resorption after oral ingestion, primarily due to the high molecular mass;
4) Fast elimination through the liver and kidneys; and
5) Lack of selectivity, due to the interaction with different receptors.

Surprisingly, it was found that the compounds according to the invention can be used as mimetics, which, as artificially produced materials, are able to exercise, in particular, the function of a protein ligand and imitate the biological effect of a peptide (agonist) or block the same (antagonist). Although the principle of providing peptide mimetics is known in the art, only very few examples of mimetics with a PPII structure have been disclosed to date, which have, however, numerous disadvantages. It came as a complete surprise that it is possible to provide structural mimetics with a central 6-ring system where the coupling of the side ring B is achieved by a central C atom, and wherein these compounds demonstrate more biologic efficacies than the known structural mimetics that have a central 7-ring system and where of the side ring is bonded to two neighboring C atoms of the central ring. It could not be anticipated and it was not obvious that these modifications would result in the possibility of using the structural mimetics according to the invention for providing molecules with very good bioavailability and very high biological efficacy that influences, for example, cell motility. When the molecules according to the invention are inserted in peptides, said peptides surprisingly demonstrate a better ability for entering the cell in comparison to known structural mimetics. In contrast to known structural mimetics, the novel structural mimetics are, for example, considerably better suited for bonding with natural bonding partners, such as the EVH1 domain. Consequently, the invention comprises completely novel and inventive structural mimetics, particularly of the polyproline II helix. The known and the novel structural mimetics differ from each other inter alia in terms of the changed position of the vinylidene group, with improved mimetic properties of the PPII helix. This results in the fact that, for ligands, for which the position of the vinylidene bridge causes a steric obstacle in the way of the bond, considerable improvements related to affinity are achieved, for example with regard to the bond with vasodilator-stimulated phosphoprotein-enabled/VASP homology 1 domain (VASP-EVH1).

Even though different approaches existed for replacing the structural motif of the PPII helix completely or in part with synthetic analogues, examining the interaction of the known structures with different protein domains was not possible at all or only with limitations. The average person skilled in the art also learns from the teaching of the prior art that the interaction of proline-rich helices with different protein domains does not have any particular biological significance. Correspondingly, the achievement of the inventors lies in the circumstance that they were able to demonstrate that this interaction and/or the modification is associated with numerous diseases, such as bacterial or viral infections, neurodegenerative disorders or the formation of tumors. Numerous mimetics that are known in the art can only be prepared with the aid of catalysts that are often difficult to remove again from the system, or that cannot be removed at all. We presently further point out that the known products have only a short shelf-life and can often only be obtained contaminated with products that are necessary for the synthesis, a circumstance that precludes them from use in the medical field altogether, or that poses great difficulty as to their use. Moreover, the binding affinity of mimetics known to date is not such that they would be able to achieve the object according to the invention.

The interaction of peptide ligands with protein receptors plays an important role in the regulation of biological processes and is crucially dependent on peptide geometry. Subject to physiological conditions, the conformation of a linear peptide is at a dynamic equilibrium, which is dependent on the pH value and the temperature, by rotation about individual bonds. As a result, only a minimal percentage of the biological reactive conformation is present.

The conformation of the peptide backbone is usually described by the three angles of φ (phi), ψ (psi) and ω (omega). Due to the partial double-bond characteristic, the peptide bond is prevented from rotating and has a planar geometry, resulting in two preferred conformations: the trans- and cis-peptide bonds, with ω=180° and/or ω=0°, wherein the trans-conformation is energetically more favorable and therefore prevalent.

This is why, for a conformation description of the peptide backbone, by way of a first approximation, the torsion angles φ and ψ of the amino acid moieties are sufficient. The angle φ, which describes the rotation along the N—$C_\alpha$ bond, is defined by the four atoms C(=O)—N—$C_\alpha$—C(=O). In the same manner, N—$C_\alpha$—C(=O)—N define the angle ψ, which describes the rotation about the $C_\alpha$—C(=O) bond. Although, in theory, a great number of different combinations is possible from φ and ψ, certain preferential conformations in peptides exist as a function of size, polarity and charge of the side chains, thus resulting in the formation of the known secondary structures, such as α-helix, β-pleated sheet, β-turn, etc.

The Amino Acid Proline as a Component in Peptides

Proline takes a special place among the twenty naturally occurring amino acids, as it is the only secondary amino acid. Due to the cyclization of the α-side chain to the amide nitrogen, the torsion angle φ=(−65±15°) is relatively restricted as component of the five-membered ring, which means, consequently, that the peptide has fewer rotational degrees of freedom. Double alkylation of nitrogen produces the result that the otherwise common amide proton is missing (in the peptide backbone), which is why proline is not a candidate for a hydrogen bridge donor; on the other hand, the carbonyl group is particularly rich in electrons, which is why it is a better hydrogen bridge acceptor than is the case with other amino acids. Due to these geometric and electronic properties, proline is unable to stabilize an α-helix ("α-helix breaker") and also does not form any β-pleated structure ("β-pleated sheet breaker"); instead, it is preferably encountered in other typical secondary structures, so-called β-turns and polyproline helix (PPII helix).

Proline-Rich Motifs and the PPII Helix as Secondary Structure

Proline-rich amino acid sequences are often encountered in proteins that participate in multi-protein complexes and that are formed and/or dissolved in the context of intracellular signal transduction processes. These proteins therein present sequences on the surfaces thereof where proline occurs exclusively or predominantly (often four and more proline units in succession).

This way, the characteristic secondary structure, which is the polyproline helix, abbreviated as PPII helix, is induced; this is understood as a stretched, left-handed helix with the torsion angles φ=−78° and ψ=+146° of the peptide backbone. As a consequence, there results a pseudo-$C_3$ rotational symmetry about the helical axis with exactly three proline moieties per rotation in cross-section (FIG. 1), which is why the proline moieties in proline-rich sequences preferably repeat at least with a periodicity of three (for example, PxxPxxP (SEQ ID No. 1) or PPxPPxPPx (SEQ ID No. 2)).

This way, the proline side chains and the carbonyl groups of the peptide backbone are exposed to the solvent at regular intervals. Due to the absence of intramolecular hydrogen bridges, the carbonyl groups are especially well suited to form intermolecular hydrogen bridge bonds with receptor proteins.

However, the structural motif of the PPII helix can also be induced when not only proline is present. The amino acid Glu occurs particularly frequently in PPII helices, as well as in the proximity thereof; however, Gln, Arg, Ala, Leu, Ser, Asp and H is are also found. The preferred binding mode between domain and ligand determines which proline positions must be strictly preserved and which can be replaced with other amino acids, if necessary.

In a preferred embodiment of the invention, the same is selected in such a manner that the bridges, which are represented by A and B, consist of 2-4 ring atoms that are selected from the group comprising C—, O—, S—and/or N-atoms. This way, rings comprising 4, 5, 6 or 7 members are obtained, which can, aside from CH2 units, also contain —O—, —S— and —N—R, wherein R=H, alkyl or acyl.

In a further preferred embodiment of the invention, the compound has the general formula 2,

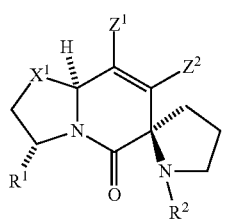

(2)

with $Z^1$, $Z^2$ as indicated in structure 1 and as shown in the configuration of the image of the structural formula 2, with $X^1$ =—$CH_2$—, —O—or —S—, and with $R^1$, $R^2$=alkyl, acyl, heteroaryl or sulfonyl.

In a further embodiment of the invention, the invention has the formula 3,

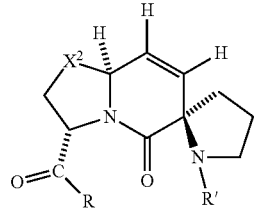

(3)

with $X^2$=—$CH_2$—, —O— or —S—, with R =NH—R", —O—R", with R"=peptidyl, substituted alkyls or heteroaryl, and with R' =acyl, peptidyl or sulfonyl.

A peptidyl is especially preferred in formula 3 R'.

According to a preferred aspect, the invention relates to the use of the named compounds as pharmaceutically active agents. The use as a pharmaceutically active agent involves applications in surgical, therapeutic or diagnostic processes.

According to a further aspect, the invention relates to a pharmaceutical substance that comprises the compounds according to the invention, if necessary, in conjunction with a pharmaceutically acceptable carrier substance.

Preferred pharmaceutical carrier substances are, for example, fillers, extenders, binders, moisteners, dissolution retarder, disintegrators, resorption accelerators, humectants, absorbers and/or lubricants.

According to a further aspect, the invention relates to the use of the compounds according to the invention as ligands for a domain selected from the group comprising SRC-homology-3 domains, WW domains, ENA-VASP homology-1 domains, GYF domains, UEV domains and/or profiline.

Correspondingly, the invention also relates to the use of novel structural mimetics of the polyproline II helix as surprisingly good inhibitors of the protein-protein interaction with particular involvement of the SH3 domains, EVH1 domains, WW domains, GYF domains, UEV domains and profiline. Proteins containing these domains, for example VASP (EVH1 domain) or YAP (WW), play inter alia a particularly important role in the regulation of cell motility (particularly VASP) and cell proliferation (particularly YAP). As such, for example, VASP is markedly overexpressed in highly invasive breast cancer cells. The interaction of YAP with the C-terminal fragment of ERBB4, which is mediated by the WW domains, results, for example, in the nuclear localization of YAP and is the prerequisite for the function of YAP as co-activator of cell proliferation. Numerous novel and surprising possibilities for use of these novel structural mimetics therefore emerge.

All of these domains preferably interact with proline-rich sequences having affinities between 1 and 500 μM, possibly requiring in certain embodiments of the invention further flanking epitopes to reach the necessary specificity. The bond between ligands, peptide and domain is preferably created by the interaction of two preformed hydrophobic surfaces. Aromatic amino acids advantageously agglomerate on the surface of the domain proteins, and whose moieties constitute a hydrophobic bonding pocket. The proline-rich peptide ligand has, due to the rigid nature of the PPII helix, a geometrically fixed, complementary structure that makes contact with the domain surface. Advantageously therein, hydrophobic contacts do not occur over the entire length of the nuclear motif that makes contact with the domain surface; rather, the ligand peptide forms an umbrella-like structure that spans over the domain. Some of the proline moieties are taken up in the hydrophobic binding pockets and thus interact with the aromatic moieties of the domain. Should these contacts be insufficient for providing biologically relevant bond strength, additional stabilizing hydrogen bridge bonds are advantageously formed, and this is made possible particularly easily by the proline's electron-rich carbonyl group.

The intermolecular bond is energetically favored because of the limited flexibility of the PPII helix, since, owing to the relatively high degree of order, the decrease of entropy is less with the bond formation than is the case with a common linear peptide. To quantify this energy contribution, it is possible to take a look at a dipeptide xP that has only two of the otherwise common four degrees of rotational freedom about the peptide backbone. Since each degree of rotational freedom at 300 K corresponds approximately to 3.5 kJ/mol, the resulting energy advantage per xP dipeptide is ca. 7 kJ/mol with complex formation.

A further affinity increase can be seen as well due to the multiple repetitions of proline-rich sequences in a single peptide, such as, for example, the bacterial surface protein ActA that bonds to the EVH1 domain (ENA-VASP homology-1 domain).

The EVH1 domain consists approximately of 115 amino acids and occurs in a variety of signal-giving multidomain proteins. Aside from a few others, this also includes the family of ENA/VASP proteins, acting as molecular adaptors and modulating the actin dynamics of the cytoskeleton. The EVH1 domains are subdivided by ligand preferences into three classes. The first class specifically recognizes, in particular, an FPPPP (SEQ ID NO: 4) nucleic motif that can be detected in all focal adhesion proteins, such as, for example, vinculin and zyxin, in lamellipodin, which can be preferably detected in lamellipodia, invadopodia and filopodia, as well as in the ActA protein of the intracellular bacterium *Listeria monocytogenes*.

To research the processes on the molecular level and the resulting biological functionality, the three-dimensional domain structure was clarified; however, the interaction with the different ligand and peptides was examined as well. It was seen therein that the EVH1 domains recognize a consensus core motif FPx$\phi$P, where phenylalanine (F) and the two outer proline positions (P) are essential for the formation of the bond, while the two inner positions still allow for variations (x=any amino acid, $\phi$=hydrophobic amino acid). This can be seen in FIG. 2, where the class-I-EVH1 domain of the human VASP protein was examined together with a short section from the ActA peptide ($_{332}$SFEFPPPPTEDEL$_{344}$) (SEQ ID No. 3). The central FPPPP motif (SEQ ID No. 4) and an affinity-increasing EL epitope are framed and show that the bond strength is clearly influenced, when the individual positions are substituted by other natural amino acids (dark=good bond, light=no bond).

The fact that positions $P_0$ and $P_1$ can be substituted by other amino acids, wherein particularly $P_0$ is completely unspecific, can be explained by the evaluation of the ligand peptide in the bonding mode: while $P_{-1}$ and $P_2$ in are taken up in a hydrophobic binding pocket of the domain, the middle two prolines are in an umbrella-like position above the domain and have almost no contact with the domain surface. The carbonyl group of the $P_0$, however, forms an essential hydrogen bridge to the NH of the tryptophan moiety W23 of the EVH1 domain.

In addition, based on a number of different test ligand peptides, it was possible to gain an overview of the bonding affinities. The highest observed bonding affinity ($K_D$=20 μM) is provided by the ligand $_{332}$SFEFPPPPTEDEL$_{344}$ (SEQ ID NO: 3), (third of the four proline-rich repeats of the ActA protein). On the other hand, when the ligands are shortened to the core motif FPPPPT (SEQ ID No. 5) thereof, no measurable affinity in relation to the VASP-EVH1 domain could be found any longer; a bond to the Mena-EVH1 domain, on the other hand, was very weak, though yet still detectable (417 μM).

A preferred embodiment of the invention provides for the use of the compounds as polyproline mimetics. Advantageously, proline-rich amino acid sequences are found, in particular, in peptides that are involved in signal transduction processes, particularly intracellular signal transduction processes. In the sense of the invention, the term mimetics can also be understood as analogues. The preferred use of the compounds according to the invention is in the treatment of diseases that are associated with a modification of the intracellular signal transduction processes, which are mediated by polyproline helix structures, selected from the group comprising bacterial infectious diseases as well as neurodegenerative and/or tumor diseases.

According to a further aspect, the invention relates to a peptide or protein comprising one or a plurality of the compounds according to the invention, wherein the compounds according to the invention are preferably used as polyproline mimetics. According to a further aspect, the invention relates to a peptide or protein comprising one or a plurality of the compounds according to the invention, as well as one or a plurality of the compounds according to structure 86.

In a preferred embodiment of the invention, the peptides are selected from a group consisting of: Ac-(SEQ ID NO: 6)-[2-Cl—F]-p-PP-(SEQ ID NO: 7)-NH$_2$, Ac-(SEQ ID NO: 6)-[2-Cl—F]-PP-p-(SEQ ID NO: 7)-NH$_2$, Ac-(SEQ ID NO: 6)-[2-Cl—F]-p-x-(SEQ ID NO: 7)-NH$_2$ and Ac-(SEQ ID NO: 6)-[2-Cl—F]-p-p-(SEQ ID NO: 7)-NH$_2$, wherein p denotes a compound according to the invention, x denotes the structure 86 and 2-Cl—F denotes 2-Cl-phenylalanine. In a further preferred embodiment of the invention, the peptides are characterized in that p=structure 85.

The structures 85 and 86 are represented in some contexts of the description of the invention as Fmoc-protected amino acid. When these structures are used in a peptide, it is preferred that the structures correspondingly do not include any Fmoc protective group(s); for example, the compounds can be bonded by a peptidyl compound to the amino acid in the peptide or protein that is located closest.

The invention also relates to the use of a compound according to the invention, a peptide or pharmaceutical agent comprising a compound according to the invention for the treatment of diseases associated with the modification of intracellular signal transduction processes, which are mediated by polyproline helix structures, preferably selected from the group comprising bacterial infectious diseases as well as neurodegenerative and/or tumor diseases.

The bacterial diseases are preferably such diseases that are associated with the following bacteria, particularly those that are mediated by the same: *legionella, streptococci, staphylococci, klebsiella, Haemophilis influenzae, rickettsia* (spotted fever), *mycobacteria, mycoplasmas, ureaplasmas, neisseria* (meningitis, Waterhouse-Friedrichsen syndrome, gonorrhea), *pseudomonads, bordetella* (pertussis), *corynebacteria* (diphtheria), *chlamydia, campylobacter* (diarrhea), *Escherichia coli, proteus, salmonella, shigella, yersinia, vibriona, enterococci, clostridien, borrelia, Treponema pallidum, brucella, francisella* and/or *leptospira*, particularly *listeria*.

Particularly preferred diseases are those that are caused by *listeria*, selected from the group comprising *L. monocytogenes* Sv1/2a, *L. monocytogenes* Sv4b F2365, *L. monocytogenes* Sv4b H7858, 178 contigs, *L. monocytogenes* Sv1/2a F6854, 133 contigs, *L. monocytogenes* Sv4b, *L. monocytogenes* Sv4a, *L. innocua* Sv6a, *L. welshimeri* Sv6b, *L. seeligeri* Sv1/2b and/or *L. ivanovii* Sv5, or that essentially instrumentally related to the afore-named preferred *listerias*.

The preferred neurodegenerative diseases are selected from the group comprising Alzheimer's disease, Parkinson's disease, Huntington's disease and/or amyotrophic lateral sclerosis (ALS).

The preferred tumor diseases are selected from the group comprising tumor diseases of the throat and neck, nose and ears, the lungs, mediastinum, gastrointestinal tract, urogenital system, gynecological system, breast, endocrine system, skin, bones and soft tissue sarcomas, mesotheliomas, melanomas, neoplasms of the central nervous system, pediatric cancers or tumor diseases, lymphomas, leukemia, paraneoplastic syndromes, metastases without known primary tumor (CUP syndrome), peritoneal carcinomastoses, immunosuppression-induced malignancies and/or metastatic tumors.

The tumors can involve, in particular, the following cancers: adenocarcinoma of the breast, prostate and large intestine; all forms of lung cancer emanating from the bronchial region; bone marrow cancer; melanoma; hepatoma; neuroblastoma; papilloma; apudo; choristoma; branchioma; malignant carcinoid syndrome; carcinoid heart disease; carcinoma (for example, Walker carcinoma, basal cell carcinoma, basosquamous carcinoma, Brown-Pearce carcinoma, ductal carcinoma, Ehrlich's tumor, in-situ carcinoma, cancer-2-carcinoma, Merkel cell carcinoma, mucous cancer, non-small cell bronchial carcinoma, oat cell carcinoma, papillary carcinoma, scirrhous carcinoma, bronchioloalveolar carcinoma, bronchial carcinoma, squamous cell carcinoma and transitional cell carcinoma); histiocytic function disturbance; leukemia (for example, in connection with B-cell leukemia, mixed-cell leukemia, null-cell leukemia, T-cell leukemia, chronic T-cell leukemia, HTLV-II-associated leukemia, acute lymphocytic leukemia, chronic-lymphocytic leukemia, mast-cell leukemia and myeloid leukemia); malignant histiocytosis, Hodgkin's disease, non-Hodgkin's lymphoma, solitary plasma cell tumor; reticuloendotheliosis, chondroblastoma; chondroma, chondrosarcoma; fibroma; fibrosarcoma; giant-cell tumors; histiocytoma; lipoma; liposarcoma; leukosarcoma; mesothelioma; myxoma; myxosarcoma; osteoma; osteosarcoma; Ewing's sarcoma; synovioma; adenofribroma; adenolymphoma; carcinosarcoma; chordoma; craniopharyngioma; dysgerminoma; hamartoma; mesenchymoma; mesonephroma; myosarcoma; ameloblastoma; cementoma; odontoma; teratoma; thymoma; chorioblastoma; adenocarcinoma; adenoma; cholangioma; cholesteatoma; cylindroma; cystadenocarcinoma; cystadenoma; granulosa cell tumor; gynadroblastoma; hidradenoma; island cell tumor; leydig cell tumor; papilloma; Sertoli cell tumor; Theka cell tumor; leiomyoma; leiomyosarcoma; myoblastoma; myoma; myosarcoma; rhabdomyoma; rhabdomyosarcoma; ependynoma; ganglioneuroma; glioma; medulloblastoma; meningioma; neurilemmoma; neuroblastoma; neuroepithelioma; neurofibroma; neuroma; paraganglioma; non-chromaffin paraganglioma; angiokeratoma; angiolymphoid hyperplasia with eosinophilia; sclerosizing angioma; angiomatosis; glomangioma; hemangioendothelioma; hemangioma; hemangiopericytoma, hemangiosarcoma; lymphoangioma, lymphoangiomyoma, lymphoangiosarcoma; pinealoma; cystosarcoma phyllodes; hemangiosarcoma; lymphoangiosarcoma; myxosarcoma; ovarian carcinoma; sarcoma (for example, Ewing sarcoma, experimentally, Kaposi sarcoma and mast-cell sarcoma); neoplasms (for example, bone neoplasms, breast neoplasms, neoplasms of the digestive system, colorectal neoplasms, liver neoplasms, pancreatic neoplasms, neoplasms of the pituitary gland, testicular neoplasms, orbital neoplasms, neoplasms of the head and neck throat, of the central nervous system, neoplasms of the hearing organ, the pelvis, the respiratory tract and urogenital tracts); neurofibromatosis and cervical squamous cell dysplasia.

In a further embodiment, the cancer or tumor is selected from the group comprising tumors of the area of the neck and throat, nose and ears comprising tumors of the inner nose, sinuses, nasopharynx, lips, oral cavity, oropharynx, larynx, hypopharynx, ear, salivary glands and paragangliomas, tumors of the lung comprising non-small cell bronchial carcinomas, small-cell bronchial carcinomas, tumors of the mediastinum, tumors of the gastrointestinal tract comprising tumors of the esophagus, stomach, pancreas, liver, gall bladder and gall ducts, small intestine, colon and rectal carcinomas and anal carcinomas, urogenital tumors comprising tumors of the kidneys, ureter, bladder, prostate, urethra, penis and testicles, gynecological tumors comprising tumors of the cervix, vagina, vulva, corpus carcinomas, malignant trophoblastic diseases, ovarian carcinoma, tumors of the fallopian tube (tuba faloppii), tumors of the abdominal cavity, mamma carcinomas, tumors of the endocrine organs comprising tumors of the thyroid, parathyroid, adrenal cortex, endocrine pancreatic tumors, carcinoid tumors and carcinoid syndrome, multiple endocrine neoplasias, bone and soft tissue sarcomas, mesotheliomas, skin tumors, melanomas comprising cutaneous and intraocular melanomas, tumors of the central nervous system, pediatric tumors comprising retinoblastoma, Wilms tumor, neurofibromatosis, neuroblastoma, Ewing sarcoma tumor family, rhabdomyosarcoma, lymphomas comprising non-Hodgkin's lymphomas, cutaneous T-cell lymphomas, primary lymphomas of the central nervous system comprising Hodgkin's lymphoma, leukemias comprising acute leukemias, chronic myeloid and lymphatic leukemias, plasma cell neoplasms, myelodysplastic syndromes, paraneoplastic syndrome, metastases without known primary tumor (CUP syndrome), peritoneal carcinomastosis, immunosuppression-induced malignancies comprising AIDS-related malignancies such as Kaposi sarcoma, AIDS-associated lymphomas, AIDS-associated lymphomas of the central nervous system, AIDS-associated Hodgkin's disease and AIDS-associated anogenital tumors, transplant-related malignancies, metastasized tumors comprising brain metastases, lung metastases, liver metastases, bone metastases, pleural and pericardial metastases as well malignant ascites.

In a further preferred embodiment, the cancer or tumor is selected from the group comprising cancers or tumor diseases of mamma carcinomas, gastrointestinal tumors, including colon carcinomas, gastric carcinomas, pancreatic carcinomas, cancer of the large and small intestines, ovarian carcinomas, cervical carcinomas, lung cancer, prostate cancer, kidney cell carcinomas and/or liver metastases.

When treating the forenamed diseases, it is particularly preferred to prepare and/or administer the pharmaceutical agent, which comprises the compounds according to the invention, as a gel, powder, tablet, controlled-release tablet, premix, emulsion, brew formulation, drops, concentrate, granules, syrup, pellets, bolus, capsule, aerosol, spray and/or inhaled agent.

Preferably, the pharmaceutical agent comprising the compounds according to the invention is present in the preparation in a concentration of 0.1 to 99.5, preferably 0.5 to 95.0, particularly preferred 20.0 to 80.0 weight %.

This preparation is preferably administered orally, subcutaneously, intravenously, intramuscularly, intraperitoneally and/or topically.

Preferably, the pharmaceutical agent containing the compounds according to the invention is administered in total quantities of 0.05 to 500 mg per kg of body weight, preferably 5 to 100 mg per kg of body weight over a 24 hour period.

Preferably, the contact is established orally, by injection, topically, vaginally, rectally and/or nasally.

The invention further relates to a kit that comprises at least one of the compounds according to the invention and/or one of the pharmaceutical agents according to the invention, if necessary with instructions for combining the contents of the kit—for example, a package insert or an internet address referring to further information on the home pages, etc. The information for handling the kit can comprise, for example, a therapy schedule for the aforementioned diseases, particularly for the preferred diseases. However, the instructions can also comprise details as to how the products according to the invention must be used, when a diagnosis of the aforementioned diseases has been made. The kit according to the invention can also be used for performing basic research.

Correspondingly, the invention also relates to the use of the kit for the prophylaxis and/or therapy of neurodegenerative diseases, bacterial infectious diseases or tumor diseases.

SEQUENCES OF THE INVENTION

SEQ ID No. 1:
PxxPxxP

SEQ ID No. 2:
PPxPPxPPx

SEQ ID No. 3:
SFEFPPPPTEDEL

SEQ ID No. 4:
FPPPP

SEQ ID No. 5:
FPPPPT

SEQ ID No. 6:
SFE

SEQ ID No. 7:
TEDEL

SEQ ID No. 8:
PPPPTEDEL

DETAILED DESCRIPTION OF THE PREFERRED EMBODIMENT

Figure 1:
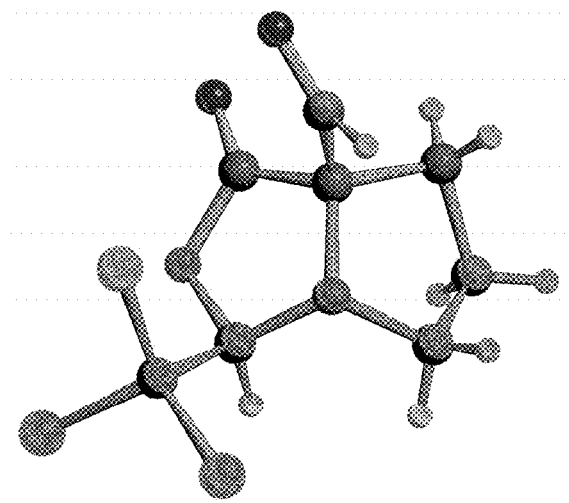
FIG. 1: Crystal structure of the aldehyde 104.
Figure 2:
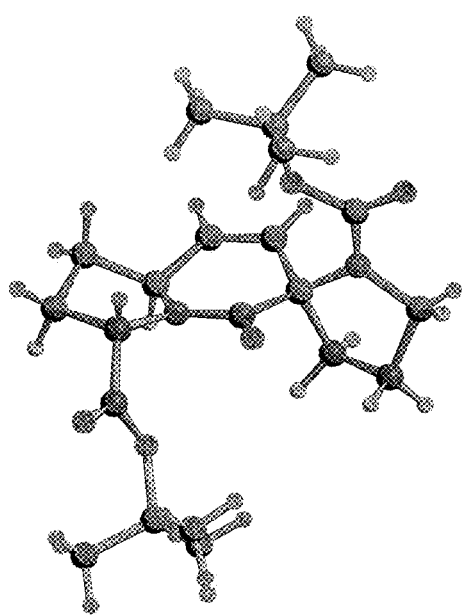
FIG. 2: Crystal structure of the bicycle 117.

The invention will be illustrated in further detail below by way of describing the synthesis of the diproline mimetic 85, while it is, however, not limited to the same.

The present invention was motivated by the search for molecules that should be able to bind with high affinity to the EVH1 domain in order to thus replace the native proline-rich sequences of the ligand peptides as bonding partner. Based on molecular modeling studies for the interaction of ligand peptides with the VASP-EVH1 domain, the compound 85 was devised, which could be inserted as a promising module (dipeptide mimetic) in test peptides in order to replace therein two neighboring proline positions of the FPPPP (SEQ ID NO: 4) core motif. Guidelines of the structural design were (1) a geometrically fixed, helical structure (tricycle); (2) optimum congruence of the bond angles and distances in comparison to those of naturally occurring proline-proline dipeptides (in the PPII helix conformation); (3) a central hydrogen bridge acceptor function in form of a carbonyl group; and (4) an amino acid-like total structure with Fmoc-protected N terminus and free C terminus to conceive a methodologically simple design for the planned insertion in peptides. The subsequently depicted molecule 85, which represents a, in terms of conformation, limited analogue of two consecutive prolines in the PPII helix, meets these requirements. By inserting the Z-configured olefin bridge, the proline rings are stabilized in the presumed biologically active conformation, the central ring of six is ensures a perfect fixation of the trans-amide bond.

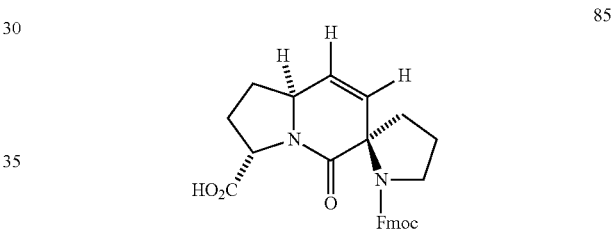

85

To provide the compound in substantial quantities, it was necessary to develop a feasible, stereoselective synthesis route. Selected as strategy was the approach of returning the target molecule in a convergent manner (retrosynthetic disintegration of the central ring of six, see diagram 20) to two vinyl-proline derivatives of the types 100 and 101. First, these could be coupled to each other by a peptide coupling prior to closing the tricycle by way of olefin metathesis. Ring closure metatheses to form rings of six have been described in the literature. The two differently substituted vinyl proline derivatives 100 and 101 in turn must each be synthesized stereoselectively. L-proline could conceivably serve as the starting material in both cases.

Diagram 20

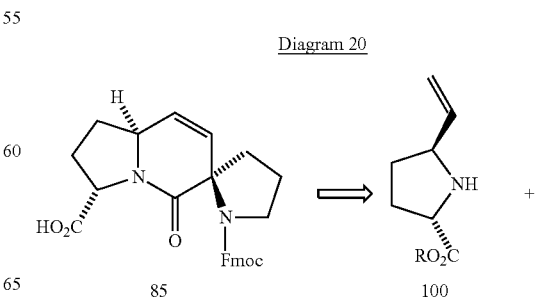

85     100

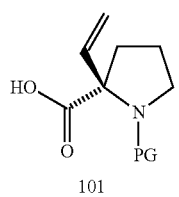

The spiro-2-vinyl-proline 107 was noted as a component of the type 101 with an N-boc-protective group. The synthesis thereof was published 2006 by Gmeiner and Bittermann (*J. Org. Chem.*, 2006, 71, 97-102.). (Diagram 31).

Protecting the L-proline with chloral resulted in the desired product 103, which was obtained as a diastereomer with a yield of 82%. Then followed a formylation; it could also be performed with a good yield of 66%. To obtain an aldehyde 104 as a pure diastereomer, most of all, it was necessary to add methyl formate extremely slowly using a dosing pump. The correct constitution and absolute configuration of the aldehyde 104 was confirmed by x-ray crystal structure analysis. The following Wittig reaction according to the published protocol reproducibly resulted in the desired product 105 with a yield of 38% (Diagram 42).

Diagram 31: Synthesis of component 107 by *Gmeiner* und *Bittermann* (*J. Org. Chem.*, 2006, 71, 97-102.).

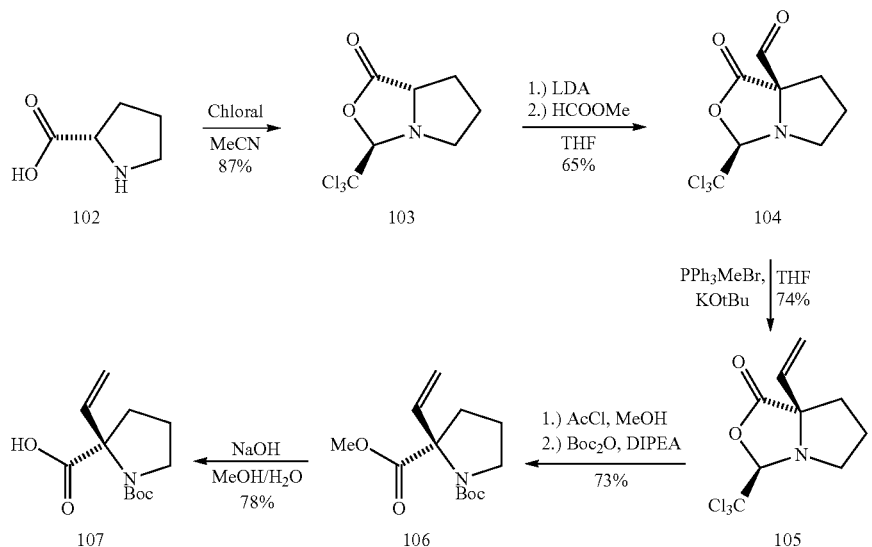

This synthesis, as published in 2006 by a third party (*J. Org. Chem.*, 2006, 71, 97-102.), was borrowed for the most part unchanged. The published protocol could be followed initially on a multi-gram-scale without encountering any major problems (Diagram 41).

Diagram 41: Synthesis of the aldehyde 104

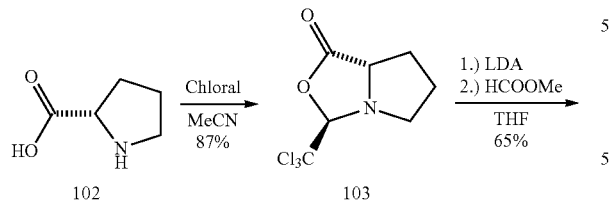

Diagram 42: Synthesis of 105 by way of the Witting reaction.

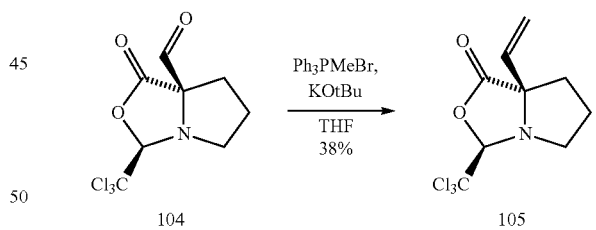

Using Nysted methylenation, it was possible to obtain the desired olefin 105 with a yield of 67% (Diagram 43)

Diagram 43: Nysted methylenation to obtain olefin 105.

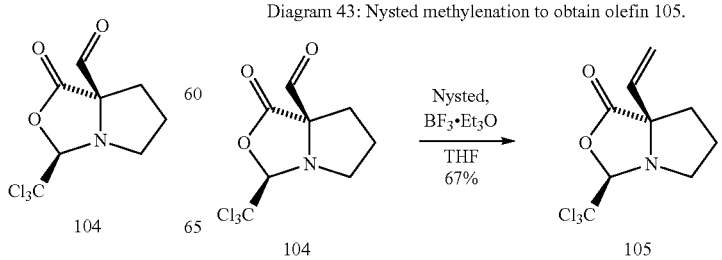

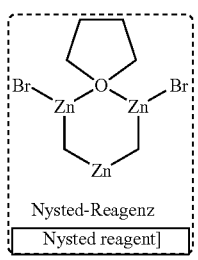

[Nysted-Reagenz / Nysted reagent]

Diagram 43: Nysted methylenation to obtain olefin 105.

The subsequent re-protection reaction into a methyl ester 106 was achieved with a satisfactory yield of 61%. A better protocol was used for cleaving the methyl ester resulting in the free acid 107 with a yield of 86%.

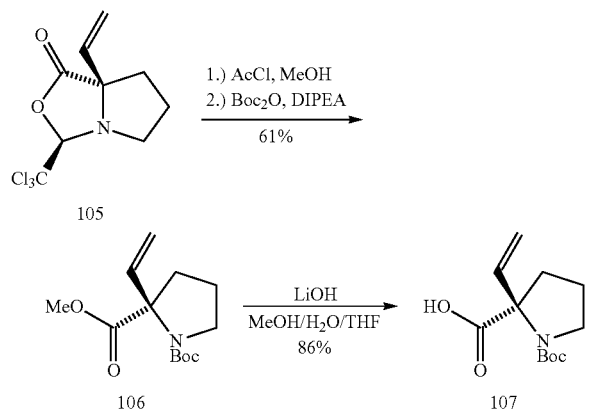

Diagram 44: Synthesis of spiro-2-vinyl-proline 107.

For the synthesis of the second component, a trans-5-vinyl-proline ester of the type 100, we relied on a synthesis that had been developed in our own laboratories (Diagram 45).

First, 50 g L-proline 102 was protected using $Boc_2O$, triethylamine and DMAP, C and N termini in a quantitative yield. The electrochemical oxidation of the protected proline 108 could be performed on the scale of 46 g (170 mmol) with an electrode area of 48×56 mm and constant current strength of 240 mA. The purification of the oxidation product resulted in high losses of the yield, which is why the same was reacted further directly, and the purification was postponed until after the cyanation to the nitrile 110. The same was performed in a 1 vol % solution of TMSOTf in DCM by dropping in 1.1 eq TMSCN, and obtained was, over two stages, a cis-trans-isomeric mixture of the cyanide 110 with a yield of 81% (d.r.: 2.9:1, cis:trans). The then following hydrogenation was done on the scale of 18 g at 80° C. under a hydrogen atmosphere with Raney nickel in a mixture of pyridine, ascetic acid and water (2:1:1), and obtained was the aldehyde 111 with a yield of 51%. The use of a hydrogen atmosphere in place of $NaH_2PO_2$ represents a clear improvement of the known methodology. A Wittig reaction, while using KHMDS as a base, resulted in the desired product 112 with a yield of 88% (d.r.: 1.7:1, cis:trans). The deprotection with TMSOTf in DCM and subsequent separation of the diastereomers by column chromatography resulted in the needed trans-configured proline 113 with a yield of 33%, as well as the cis-epimer 114 (not shown) with a yield of 49%.

With the thus obtained material, the further synthesis of the tricyclic diproline mimetics was explored (peptide coupling and subsequent ring closure metathesis). Despite the steric obstacle posed by the two vinyl groups (particularly the spirocyclic component 107), it was possible to successfully couple the peptide bond using HATU in NMP at 85° C. The carboxylic acid 107 therein was pre-activated with HATU, prior to adding the amine 113 and diisopropylethylamine as base. The identity of the coupling product could be confirmed in the $^1$H-NMR spectrum despite the presence of a rotameric mixture.

Diagram 45: Synthesis of the trans-5-vinyl-proline derivatives.

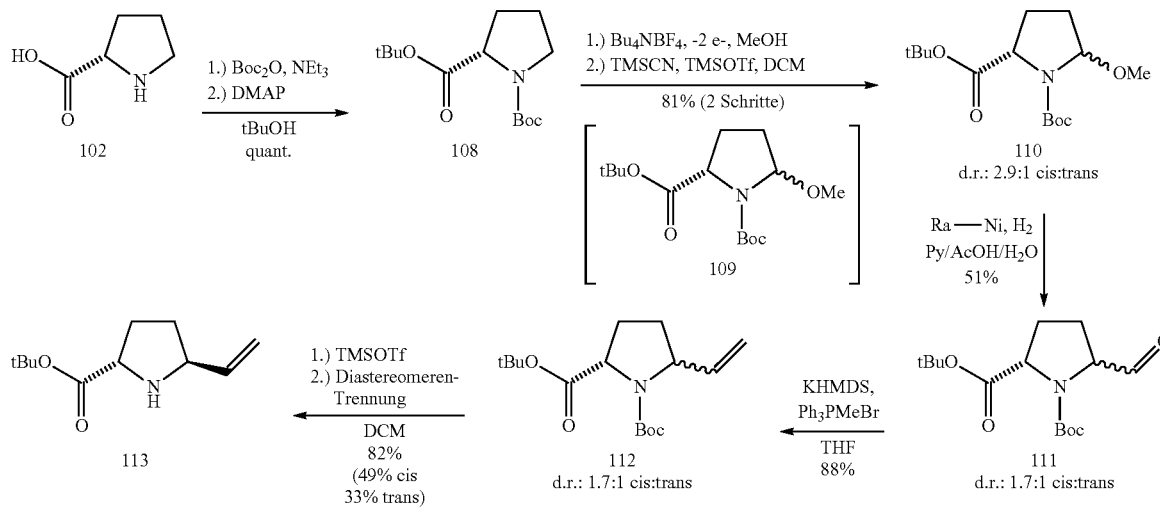

[Diastereomeren-Trennung = diastereomer separation; 2 Schritte = two steps]

Diagram 46: Peptide coupling of the vinyl-prolines 113 and 107 using HATU

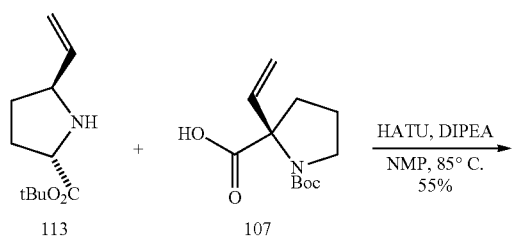

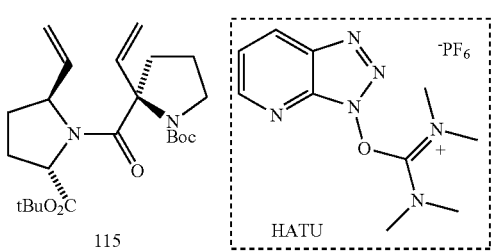

Diagram 53: Ring closure metathesis to arrive at the tricycle 117.

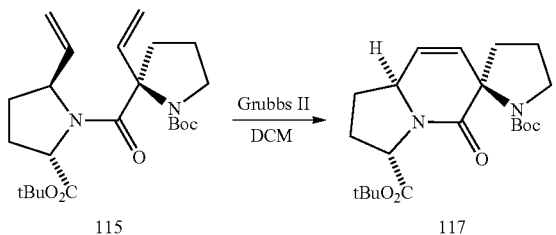

To prepare the tricycle 117 by way of a ring closure metathesis, Grubbs' catalyst, generation II (30 mol-%) was first added to the dipeptide 115 (Diagram 53), and the substance was heated for 7 hours to 50° C. (300 W) in a microwave. The desired product 117 was obtained with a yield of 54%. In addition, 22% of the edukt 115 could be re-isolated. The success of the ring closure metathesis could be clearly documented in the $^1$H-NMR spectrum, by way of the change of the olefin signals. Moreover, the structure and configuration of the tricycle 117 could be documented by way of x-ray diffractometry.

To render the synthetized tricycle 117 usable in the context of the solid phase peptide synthesis, both protective groups finally had to be cleaved, and the amine function had to be provided with an Fmoc protective group. This is the only N-type protective group of any practical significance that can be cleaved under mild basic conditions, and for which purpose secondary amines, such as piperidine, morpholine, inter alia, are typically used. This way, it is possible to generate the unprotected amino function in the solid phase synthesis without additionally producing salts. The increased base instability compromises the use of the Fmoc group in the organic synthesis and therefore requires changing the protective group in a late stage.

Diagram 54: Fmoc protection relative to the target structure 85.

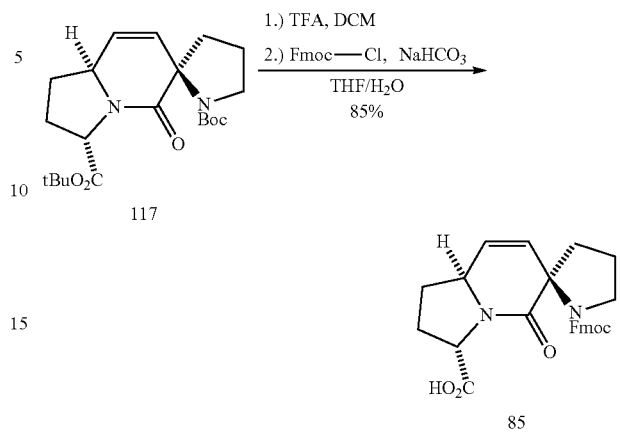

Figure 3:
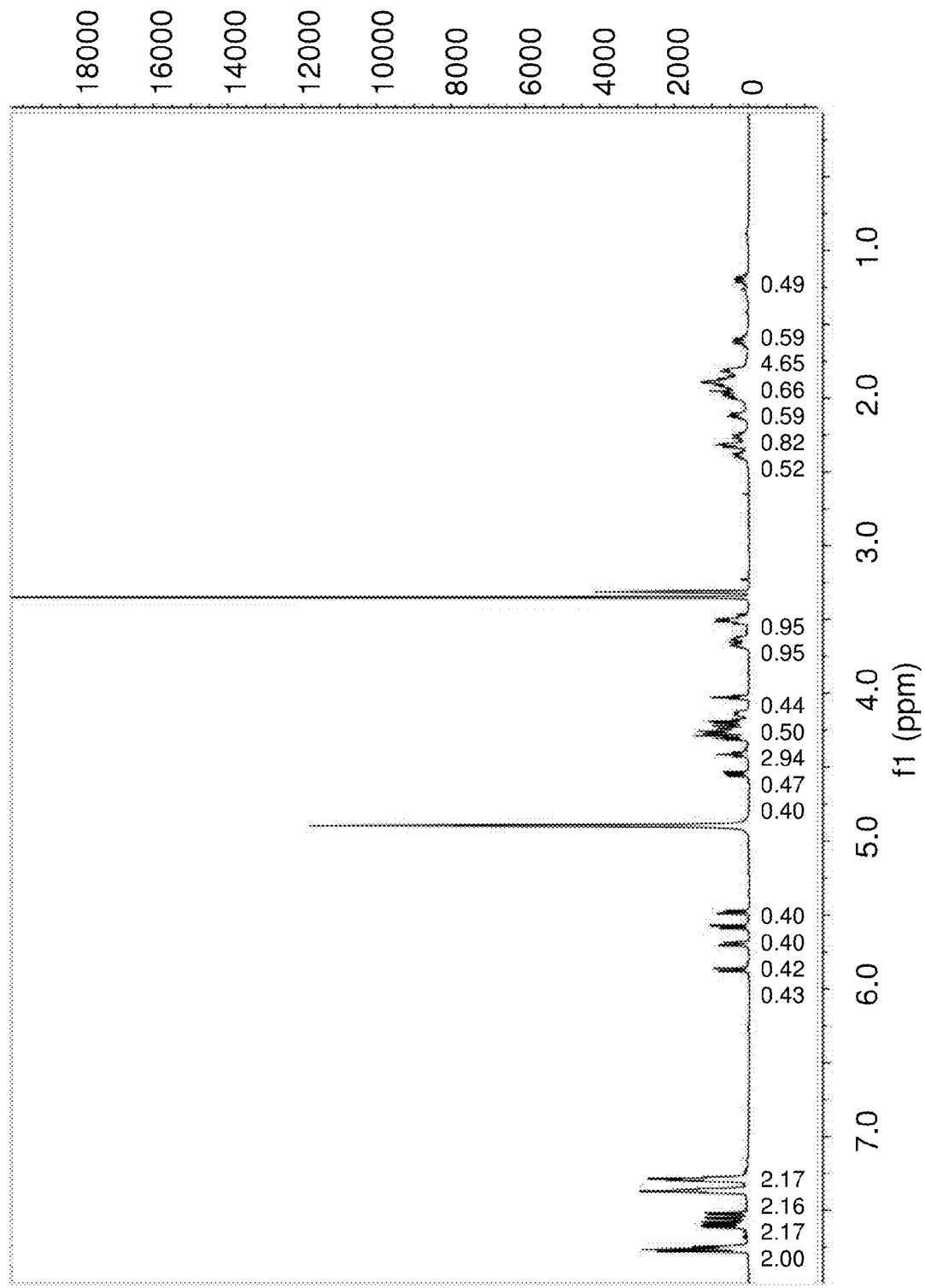
FIG. 3: $^1$H-NMR spectrum of the diproline component 85 (600 MHz, MeOH-d$^4$, RT).

An excess of trifluoroascetic acid (99%) in dichloromethane was added to 115 for the joint cleaving of the Boc-protective group and the tert-butyl ester by acid. The substance was then stirred at room temperature (Diagram 54). Subsequently, under Schotten-Baumann conditions, the residue was transferred into the Fmoc-protected end product 85. Said product proved markedly polar but could nevertheless be extracted with dichloromethane from the aqueous phase with a pH≈1, followed by purification via column chromatography on silica gel. 85 was obtained as an amorphous, muted white solid material (85%), whose NMR spectra matched expectations (see FIG. 3 for 600 MHz $^1$H-NMR spectrum (MeOH-d$^4$), 60:40 rotameric mixture).

Figure 4:
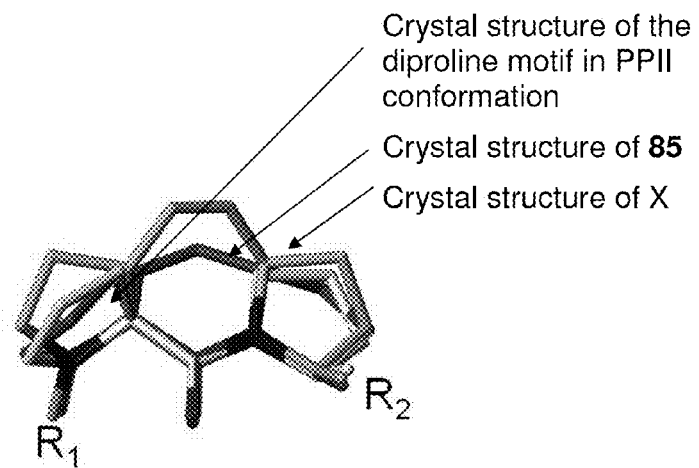
FIG. 4: Comparison of the crystal structure of 85 with a diproline motif in PPII conformation, as well as the crystal structure of X. A, side view; B, top view.
Figure 4:
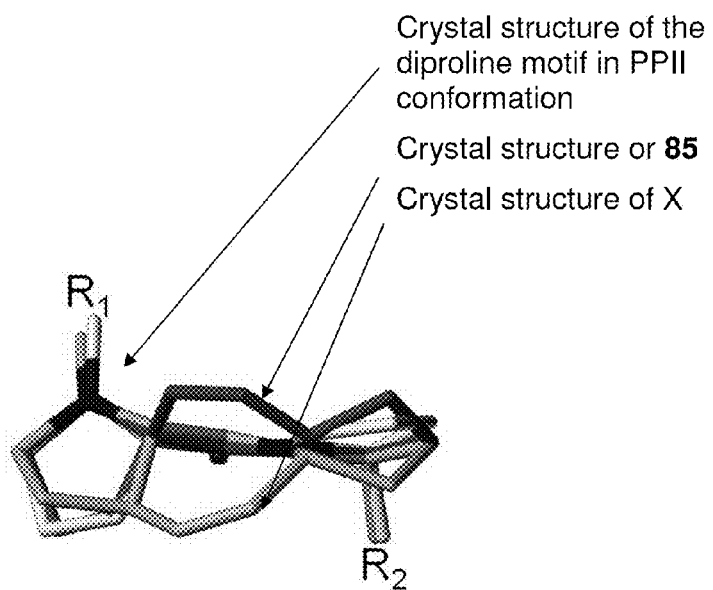

Substances According to the Invention as Diproline Mimetics in PPII Conformation The comparison of the crystal structure of 85 with a diproline motif in PPII conformation as well as the crystal structure of X, wherein X denotes the already known PPII-mimetic amino acid, is depicted in FIG. 4 (FIG. 4).

It can be seen clearly that all three structures are identical with regard to the position of R1 and R2 as well as the middle carbonyl group; plus, the positions of the pyrrolidine rings match those of the diproline motif, taking into account the proline pucker. The compounds according to the invention differ substantially, however, in the position of the vinylidene bridge in comparison to that described previously. This property is the main reason for the surprising novel binding properties of type 85 on protein surfaces.

Biological Results

These results are particularly remarkable insofar as these are experiments that have not been described to date for the EVH1 domain, and insofar as they lead to a number of important findings that can be summarized as shown below, thereby offering a foundation for further research:

1) The insertion of the synthetically prepared tricycle 85 in different test peptides under standard coupling condition (DIC/HOBt) of the solid-phase peptide synthesis was achieved without problems.
2) The prediction of the reactive conformation when binding the PPII helix to the EVH1 receptor is confirmed by the good bonding affinity of the ligand peptide I; and/or the biologically needed conformation and the actual conformation of the tricycle 85 match well.
3) The expected beneficial entropy effect by local, conformational pre-fixation of the ligand seems to confirm itself based on the found higher bonding affinity in comparison to the native peptide sequence. On the other hand, the geometric fixation also does not prevent the convergence of the ligand and domain protein, and thereby the bond formation.

Initial Biological Results and Outlook
Bonding to the EVH1 Domain

With the aid of the synthetic compound 85, by way of an example, the ligand peptides were synthetized with partially or completely substituted proline sequences and then examined for their interaction with the EVH1 domain (p=component 85). It was found therein that, due to the insertion of the mimetic 85, it was possible to increase the bonding affinity of the ligand peptides relative to the domain. When exchanging all prolines with interconnected components of 85 and the PPII-mimetic component 86, the result are ligand peptides with considerably improved affinity in comparison to that of the native peptide.

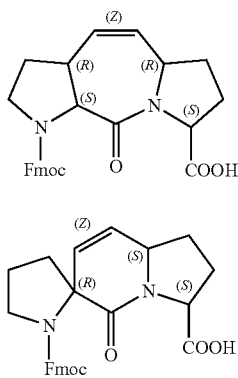

This is summarized in Table 1 below, which lists the bonding affinities of the ligand peptides as well as of the underlying native peptide ligands.

TABLE 1

| Ligand | $K_D$ (fluorescence titration) | $K_D$ (ITC) |
| --- | --- | --- |
| Ac-(SEQ ID NO: 6)-[2-Cl-F]-(SEQ ID NO: 8)-NH$_2$ | 5 µM | 2 µM |
| Ac-(SEQ ID NO: 6)-[2-Cl-F]-p-x-(SEQ ID NO: 7)-NH$_2$ | 280 nM | 370 nM |

(p: component 85; x: component 86)

The bonding affinities were determined by means of fluorescence titration and isothermal calorimetry (p=component 85, wherein x denotes the already known PPII-mimetic amino acid according to structure 86 (presently as Fmoc-protected amino acid); and "2-Cl—F" stands for 2-Cl-phenylalanine).

Further experiments demonstrate that inserting the mimetic 85 will improve the bonding affinity of the ligand peptide relative to the domain (VASP-EVH1):

```
Ac-(SEQ ID NO: 6)-[2Cl-F]-PP-x-
(SEQ ID NO: 7)-NH2
Kd = 0.77 uM

Ac-(SEQ ID NO: 6)-[2-Cl-F]-x-x-
(SEQ ID NO: 7)-NH2
Kd = 0.86 uM

Ac-(SEQ ID NO: 6)-[2-Cl-F]-p-x-
(SEQ ID NO: 7)-NH2
Kd = 0.37 uM
```

In addition, the observed increase in affinity with the compounds according to the invention allows for the first time ever to forego using natural amino acids completely, while still preserving the ability to bind to the EVH1 domains:
Ac-[2-Cl—F]-p-x-OH Kd=3 uM In comparison, for the correspondingly abbreviated ActA-derived peptide Ac-(SEQ ID NO: 4)-OH, it was not possible to document a Kd value within the measuring range up to 500 uM.

Cellular Take-Up of EVH1 Inhibitors

Figure 5:
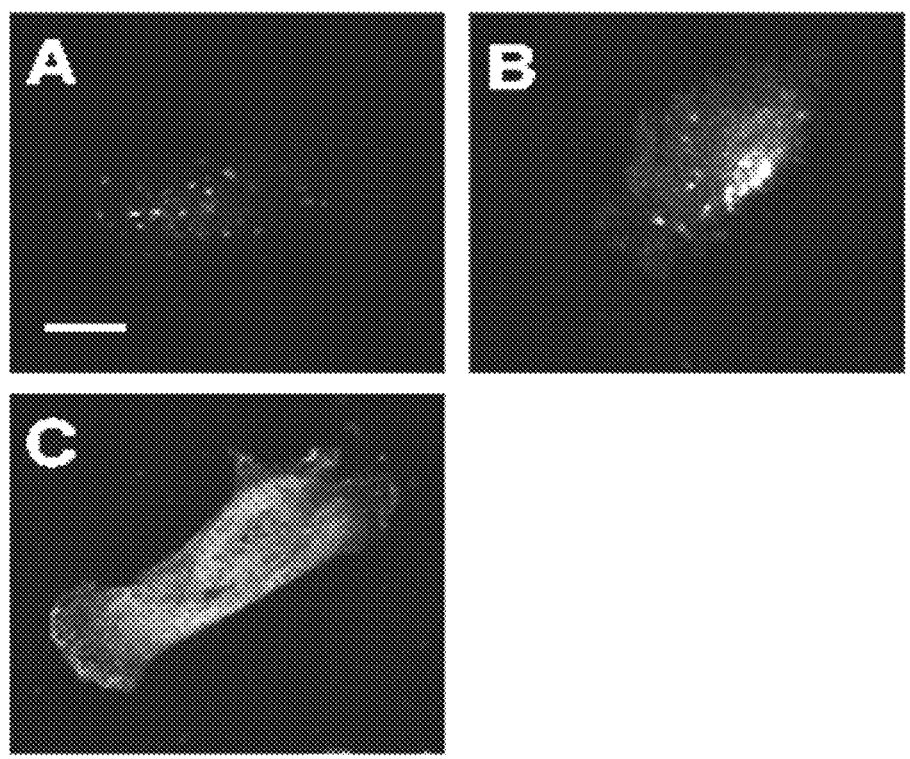
FIG. 5: Cellular take-up of the EVH1 inhibitors. (A) Control without ligands; (B)+NBD-(SEQ ID NO: 3)-NH$_2$ (C)+NBD-(SEQ ID NO: 6)-[2-Cl—F]-p-x-(SEQ ID NO: 7)-NH$^2$

Introducing the compounds according to the invention resulted in a changed take-up of the EVH1 inhibitors into the cell as an essential prerequisite for their activity as inhibitors for the interactions from protein to protein. It could be demonstrated that, contrary to the fluorescence-labeled ActA-derived peptide NBD-(SEQ ID NO: 3)-NH$_2$, the corresponding peptide NBD-(SEQ ID NO: 6)-[2-Cl—F]-px-(SEQ ID NO: 7)-NH$_2$ could be detected in visibly elevated concentration [in] MDA-MB-231 cells (FIG. 5).

Since the general concept with regard to the synthesis and the biological use of the target structure 85 could be implemented successfully, based on this promising foundation, numerous further possibilities are now conceivable for addressing relevant protein domains that bond polyproline-containing ligands in a targeted fashion in that they employ small synthetic molecules. Aside from varying existing molecule structures, it would also be conceivable to extend the concept to include the synthesis of ligands for other domains (MENA-, ENA- and EVL-EVH1, WW, SH3 inter alia), to provide combinations with other proline-mimetic scaffolds, as well as execute the complete substitution of polyproline motifs by lining up 85 in a sequence.

Experimental Part

Glass instruments were evacuated 3× on a vacuum/argon dual faucet apparatus in an oil pump vacuum with a final pressure of 0.2-2 mbar, heated with a propane gas burner and subsequently ventilated with argon. Disposable syringes, cannulas and transfer cannulas were stored, wet from acetone, inside a drying cabinet at 80° C. Solvents were removed in a vacuum rotation evaporator, by the company Bčhi, at a pressure of 1013-10 mbar and a water bath temperature of 40° C.

THF, toluene and diethylether were refluxed for several hours under argon and over sodium, with benzophenone as indicator, chloroform over phosphorous pentoxide and dichloromethane over calcium hydride, and then distilled. Methanol was refluxed over magnesium and iodine then distilled. THF, methyl THF, toluene, diethylether and dichloromethane were freshly distilled prior to use. Non-dehydrated solvents were also distilled prior to use. The remaining reagents were purchased from the companies ABCR, Acros, Aldrich, Chemetall, Fluka, Merck, Lancaster, Riedel-de Haen and Strem and used without further purification.

Separation processes by way of column chromatography were done on silica gel 60 (230-400 mesh, Merck) or aluminum oxide (50-200 µm, Brockmann I, Acros). Methanol, dichloromethane, ethylacetate and cyclohexane were distilled prior to use. Mobile phases are indicated in volume fractions.

The IR spectra were recorded at room temperature on an FT-IR Paragon 1000 instrument by the company Perkin-Elmer, with ATR engineering on a ZnSe crystal, to which the substances were applied by way of solutions. The absorptions are indicated in wave numbers v in cm-1 and characterized with s (strong), m (medium), w (weak). If necessary, a br (wide signal) is added to this.

Any methanol used for preparative electrolysis processes was distilled prior to use. Linear laboratory power equipment VLP-1602 Pro by der Firma Voltcraft and 48×28 mm graphite plate electrodes by the company Didac-Tec served as sources of voltage.

The melting points were determined with a Melting Point B-545 by the company Büchi and with a PolyTherm A micro heating bench system by the company Wagner and Munz.

$^1$H and $^{13}$C-NMR spectra were recorded at room temperature on the Avance DPX 300, AC 300, AV 400, Avance DPX 500 and AV 600 instruments, by the company Bruker. Chemical shifts are indicated as ppm relative to the signals of the used solvents ($^{13}$C-NMR) and/or relative to non-deuterated traces of these solvents ($^1$H-NMR) (CHCl$_3$)=7.24 ppm, (CDCl$_3$)=77.00 ppm, (CD$_2$HOD)=3.31 ppm, (MeOD)= 49.05 ppm.

In the $^1$H-spectra, multiplicities are described as:
s=singlet
d=doublet
t=triplet
q=quadruplet
sept=septet
m=multiplet.

The $^{13}$C nuclear magnetic resonance spectra were recorded as APT and described with
s=quartary C atom
d=tertiary C atom
t=secondary C atom
q=primary C atom.

the coupling constants J are indicated in Hertz. The assignments of the NMR signals were substantiated with H,H-COSY, TOCSY, HMBC and HMQC-spectra. The numbering of the carbon atoms that was chosen for the assignment can be derived from the respective figures and does not necessarily coincide with IUPAC nomenclature.

The DC was performed on Merck films HX616606 (20×20 mm, 0.2 mm layer thickness). All eluent mixtures are indicated in volume parts. Any staining was done by means of an UV lamp, potassium permanganate solution or cer[ium] (IV) sulfate solution and subsequent heating with a hot-air dryer.

Low resolution (LR) MS spectra were recorded on a Finnigan MAT Incos 50 Galaxy System (GC/DIP-MS) with an Optima 5-capillary column and hydrogen as carrier gas, as well as a combined HP6890/MSD5973 (GC-MS) system by the company Agilent Technologies and an HP5 capillary column. The ionization of the sample occurred per EI at 70 eV. The fragments were indicated in m/z; the intensity of the signals refers to the most intensive peak at 100%.

High resolution (HR) MS spectra were measured on a Finnigan MAT HSQ-30 by the DIP method. The ionization occurred at 70 eV according to the EI or ESI method.

The rotational values were measured in a cuvette of a length of 10 cm on a polarimeter 343 by the company Perkin-Elmer. The concentrations are indicated in g ‡ (100 ml)$^{-1}$.

X-ray crystal structure analyses were performed on a Nonius Kappa CCD diffractometer.

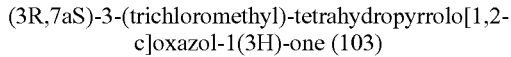

(3R,7aS)-3-(trichloromethyl)-tetrahydropyrrolo[1,2-c]oxazol-1(3H)-one (103)

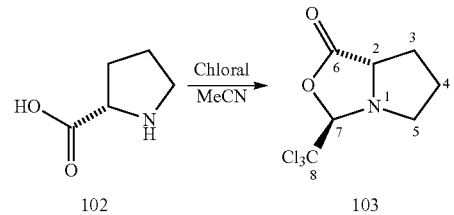

22 ml (225 mmol, 2.5 eq) chloral was added to a suspension of 10.470 g (90.94 mmol, 1.0 eq) L-proline (102) in 45 ml MeCN at RT, and the obtained solution was stirred for 19.5 h at RT. The solvent was removed at reduced pressure and the residue dissolved and filtered in 100 ml DCM. The filtrate was concentrated, and this process was repeated three more times. 18.141 g (74.20 mmol, 82%) of the product 103 was obtained as a white solid.

M (C$_7$H$_8$Cl$_3$NO$_2$): 244.50 g mol$^{-1}$.
$[\alpha]^{20}_D$:34.3° (c=(0.970, benzene).
Melting point: 109.6° C.
$^1$H-NMR (400 MHz, CDCl$_3$): δ=1.78-1.64 (m, 1H, H4'), 1.96-1.85 (m, 1H, H4), 2.13-2.02 (m, 1H, H3'), 2.26-2.13 (m, 1H, H3), 3.15-3.06 (m, 1H, H5'), 3.39 (ddd, J 10.9, 7.8, 6.0, 1H, H5), 4.09 (dd, J 8.9, 4.6, 1H, H2), 5.14 (s, 1H, H7).
$^{13}$C-NMR (100 MHz, CDCl$_3$: δ=25.32 (t, C4), 29.91 (t, C3), 57.87 (t, C5), 62.38 (t, C2), 100.62 (s, C8), 103.60 (d, C7), 175.43 (s, C6).
IR (FT-ATR): ν=2958 (m), 2920 (w), 2893 (w), 2866 (w), 1784 (s), 1725 (m), 1449 (w), 1373 (w), 1359 (w), 1322 (m), 1283 (m), 1270 (m), 1243 (m), 1174 (s), 1107 (s), 1083 (m), 1043 (w), 1001 (s), 958 (s), 913 (w), 898 (m), 838 (s), 813 (s), 790 (s), 744 (s).
Crystal Data

| | | |
|---|---|---|
| Identification code | Z2 | |
| Empirical formula | C7 H8 Cl3 N O2 | |
| Formula weight | 244.49 | |
| Temperature | 100(2) K | |
| Wavelength | 0.71073 A | |
| Crystal system, space group | Orthorhombic, P212121 | |
| Unit cell dimensions | a = 8.5642(6) A | alpha = 90 deg. |
| | b = 8.8955(4) A | beta = 90 deg. |
| | c = 12.9294(11) A | gamma = 90 deg. |

| | |
|---|---|
| Volume | 985.00(12) Å$^3$ |
| Z, Calculated density | 4, 1.649 Mg/m$^3$ |
| Absorption coefficient | 0.895 mm$^{-1}$ |
| F(000) | 496 |
| Crystal size | .3 × .3 × .2 mm |
| Theta range for data collection | 2.78 to 26.99 deg. |
| Limiting indices | −8 ≤ h ≤ 10 −9 ≤ k ≤ 11 −16 ≤ l ≤ 10 |
| Reflections collected/unique | 3966/2109 [R(int) = 0.0254] |
| Reflection observed [I > 2sigma(I)] | 1902 |
| Completeness to theta = 26.99 | 99.9% |
| Absorption correction | None |
| Refinement method | Full-matrix least-squares on F$^2$ |
| Data/restraints/parameters | 2109/0/150 |
| Goodness-of-fit on F$^2$ | 1.020 |
| Final R indices [I > 2sigma(I)] | R1 = 0.0292, wR2 = 0.0547 |
| R indices (all data) | R1 = 0.0354, wR2 = 0.0562 |
| Absolute structure parameter | −0.04(5) |
| Largest diff. peak and hole | 0.258 and −0.354 e.Å$^{-3}$ |

(3R,7aR)-1-oxo-3-(trichloromethyl)-hexahydropyrrolo[1,2-c]-oxazol-7a carbaldehyde (104)

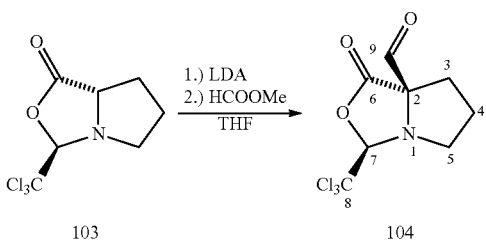

After adding approximately 3.5 g LiCl bei −78° C. to a solution of 14.092 g (57.64 mmol, 1.0 eq) of the protected proline 103, 138 ml (86.46 mmol, 1.5 eq, 0.625 M) LDA in THF were dropped in over the course of 60 min. The solution was stirred for 30 min at this temperature, and then 15 ml (241.85 mmol, 4.0 eq) HCOOMe was very slowly dropped in over 120 min. The solution was stirred for another 30 min at −78° C., and then brought to a temperature of −40° C. over the course of 1 h. 120 ml of a 10% citric acid solution in water was then added, the substance was extracted 3× with 120 ml MTBE respectively, and the combined organic phases were washed with 500 ml saturated NaCl solution, dried over magnesium sulfate, and the solvent was removed under reduced pressure. Chromatography on silica gel with EtOAc/CyHex 1:4 as eluent yielded 10.388 g (38.12 mmol, 66%) of the product 104 as white solid.

M (C$_8$H$_8$Cl$_3$NO$_3$): 272.51 g mol$^{-1}$.
DC: R$_f$=0.13 (EtOAc/CyHex 1:4).
[α]$^{25}_D$: 29.9° (c=0.520, CHCl$_3$).
Melting point: 84.8° C.
$^1$H-NMR (300 MHz, CDCl$_3$): δ=2.00-1.77 (m, 2H, H4), 2.44-2.20 (m, 2H, H3), 3.31 (dt, J 11.6, 6.0, 1H, H5'), 3.52 (ddd, J 11.4, 7.7, 6.3, 1H, H5), 5.16 (s, 1H, H7), 9.59 (s, 1H, H9).
$^{13}$C-NMR (75 MHz, CDCl$_3$): δ=25.47 (t, C4), 33.84 (t, C3), 58.94 (t, C5), 78.01 (s, C2), 99.92 (s, C8), 102.36 (d, C7), 169.27 (s, C6), 193.43 (d, C9).
GC-MS: m/z=272 ([M]$^+$, 1), 242 ([M]$^+$-CHO, 20), 117 (24), 96 (59), 68 (35), 41 (100).
IR (FT-ATR): ν=3017 (w), 2914 (w), 2846 (w), 1807 (m), 1729 (w), 1456 (w), 1353 (w), 1319 (w), 1272 (w), 1213 (m), 1190 (w), 11343 (w), 1107 (w), 1058 (w), 1020 (w), 993 (w), 972 (w), 929 (w), 839 (w), 816 (w), 747 (s), 667 (m).
Crystal Data

| | | |
|---|---|---|
| Identification code | zz | |
| Empirical formula | C8 H8 Cl3 N O3 | |
| Formula weight | 272.50 | |
| Temperature | 100(2) K | |
| Wavelength | 0.71073 Å | |
| Crystal system, space group | Triclinic, P1 | |
| Unit cell dimensions | a = 6.0569(8) Å | alpha = 70.252(7) deg. |
| | b = 6.9158(10) Å | beta = 87.601(10) deg. |
| | c = 7.9722(10) Å | gamma = 64.141(9) deg. |
| Volume | 280.63(7) Å$^3$ | |
| Z, Calculated density | 1, 1.612 Mg/m$^3$ | |
| Absorption coefficient | 0.801 mm$^{-1}$ | |
| F(000) | 138 | |
| Crystal size | .2 × .2 × .07 mm | |
| Theta range for data collection | 2.74 to 26.99 deg. | |
| Limiting indices | −7 ≤ h ≤ 6 −8 ≤ k ≤ 7 −10 ≤ l ≤ 9 | |
| Reflections collected/unique | 1616/1616 [R(int) = 0.0000] | |
| Reflection observed [I > 2sigma(I)] | 1538 | |
| Completeness to theta = 26.99 | 95.6% | |
| Absorption correction | None | |
| Refinement method | Full-matrix least-squares on F$^2$ | |
| Data/restraints/parameters | 1616/3/168 | |
| Goodness-of-fit on F$^2$ | 1.051 | |
| Final R indices [I > 2sigma(I)] | R1 = 0.0241, wR2 = 0.0573 | |

| | |
|---|---|
| R indices (all data) | R1 = 0.0262, wR2 = 0.0583 |
| Absolute structure parameter | 0.02(5) |
| Largest diff. peak and hole | 0.202 and −0.239 e.Å$^{-3}$ |

(3R,7aR)-3-(trichloromethyl)-7a-vinyltetrahydropyrrolo[1,2-c]oxazol-1-(3H)-one (105)

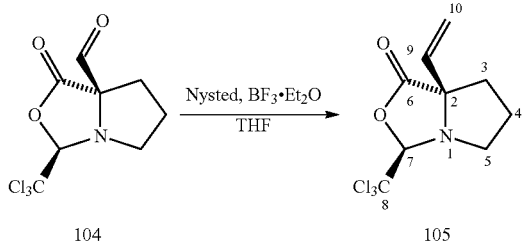

First, 6 ml (42.23 mmol, 2.5 eq) BF$_3$·Et$_2$O in 50 ml THF was dropped to a suspension of 97 g (42.23 mmol, 2.5 eq) Nysted reagent (50 w % in THF, Aldrich) in 130 ml THF over the course of 20 min at 0° C., and then 4.603 g (16.89 mmol, 1.0 eq) of the educt 104 in 30 ml THF was dropped to this substance. The reaction mixture was stirred for 2 h at RT and extracted 3× with 200 ml n-hexane, respectively, following the addition of 200 ml 1 N HCl solution. The combined organic phases were dried over magnesium sulfate; the solvent was removed at reduced pressure and yielded, after chromatography on silica gel with EtOAc/CyHey 1:10 as eluent, 3.051 g (11.28 mmol, 67%) of the product 105 as colorless oil.

M (C$_9$H$_{10}$Cl$_3$NO$_2$): 270.54 g mol$^{-1}$.
DC: R$_f$=0.17 (EtOAc/CyHex 1:10).
[α]$^{22}_D$:49.9° (c=0.660, CHCl3).
Melting point: 84.8° C.
$^1$H-NMR (300 MHz, CDCl$_3$): δ=2.00-1.77 (m, 2H, H4), 2.44-2.20 (m, 2H, H3), 3.31 (dt, J 11.6, 6.0, 1H, H5'), 3.52 (ddd, J 11.4, 7.7, 6.3, 1H, H5), 5.16 (s, 1H, H7), 9.59 (s, 1H, H9).
$^{13}$C-NMR (75 MHz, CDCl$_3$: δ=25.47 (t, C4), 33.84 (t, C3), 58.94 (t, C5), 78.01 (s, C2), 99.92 (s, C8), 102.36 (d, C7), 169.27 (s, C6), 193.43 (d, C9).
GC-MS: m/z=272 ([M]$^+$, 1), 242 ([M]$^+$-CHO, 20), 117 (24), 96 (59), 68 (35), 41 (100).
IR (FT-ATR): ν=3017 (w), 2914 (w), 2846 (w), 1807 (m), 1729 (w), 1456 (w), 1353 (w), 1319 (w), 1272 (w), 1213 (m), 1190 (w), 11343 (w), 1107 (w), 1058 (w), 1020 (w), 993 (w), 972 (w), 929 (w), 839 (w), 816 (w), 747 (s), 667 (m).

(R)-1-tert-butyl-2-methyl-2-vinylpyrrolidine-1,2-dicarboxylate (106)

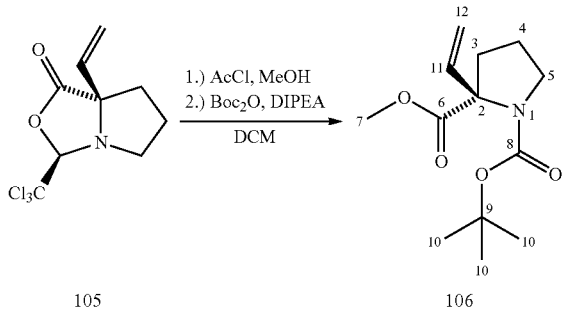

First, 15 ml (212.24 mmol, 10 eq) AcCl was added to 60 ml MeOH at 0° C., which was followed by the addition of a solution of 5.763 g (21.30 mmol, 1.0 eq) of the educt 105 in 20 ml MeOH. The solution was stirred for 7 days at RT; afterwards the solvent was removed at reduced pressure, the residue was taken up in 20 ml MeOH, and the solvent was removed once again at reduced pressure. The residue was then taken up in 60 ml DCM, 17.20 ml (106.50 mmol, 5.0 eq) DIPEA was added, and then a solution of 17.7 ml (82.72 mmol, 3.9 eq) Boc$_2$O in 35 ml was dropped in. The substance was stirred for 2.5 days at RT, the solvent removed at reduced pressure, and the residue was taken up in 100 ml MTBE. The ether phase was washed in succession with 100 ml each of 1 N HCl solution, saturated NaHCO$_3$ solution and saturated NaCl solution, dried over magnesium sulfate, the solvent was then removed at reduced pressure and, following chromatography on silica gel with EtOAc/CyHex 1:6 as eluent, 3.654 g (14.31 mmol, 67%) of the protected vinyl proline 106 was obtained as colorless oil.

M (C$_{13}$H$_{21}$NO$_4$): 255.31 g mol$^{-1}$.
DC: R$_f$=0.20 (EtOAc/CyHex 1:4).
[α]$^{22}_D$: 62.5° (c=0.455, CHCl$_3$).
$^1$H-NMR (300 MHz, CDCl$_3$): δ=1.38 (Ψ-d, J 28.5(Ψ), 9H, H10), 1.90-1.74 (m, 2H, H4), 2.03-1.91 (m, 1H, H3'), 2.25-2.08 (m, 1H, H3), 3.67-3.46 (m, 2H, H5), 3.71 (Ψ-d, J1.7(Ψ), 3H, H7), 5.02 (Ψ-dd, J 17.0, 4.6(Ψ), 1H, H12'), 5.13 (Ψ-dd, J 10.5, 4.2(Ψ), 1H, H12), 6.30 (Ψ-ddd, J 17.2, 10.5, 3.8(Ψ), 1H).
$^{13}$C-NMR (75 MHz, CDCl$_3$: δ=22.76/21.87 (t, C4), 28.38/28.18 (q, C10), 39.19/37.93 (t, C3), 47.99/47.82 (t, C5), 52.39/52.20 (q, C7), 69.45/69.30 (s, C2), 79.97/79.72 (s, C9), 113.08/112.96 (t, C12), 137.15/136.39 (d, C11), 153.55/153.44 (s, C8), 173.72 (s, C6).
GC-MS: m/z=196 ([M]$^+$-C$_2$H$_3$O$_2$, 13), 140 (75), 96 (63), 56 (100).
IR (FT-ATR): ν=3085 (w), 2974 (m), 2876 (w), 1742 (s), 1696 (s), 1641 (w), 1476 (w), 1453 (w), 1432 (w), 1387 (s), 1364 (s), 1289 (w), 1258 (s), 1214 (m), 1165 (s), 1122 (s), 1071 (m), 1021 (w), 989 (w), 959 (w), 933 (w), 921 (w), 881 (w), 857 (w), 784 (w), 770 (w), 741 (w), 663 (w).
HR-MS: (ESI, C$_{13}$H$_{21}$NNaO$_4$): 278.137±0.003 u (278.1368 u).

(R)-1-(tert-butoxycarbonyl)-2-vinylpyrrolidine-2-carboxylic acid (107)

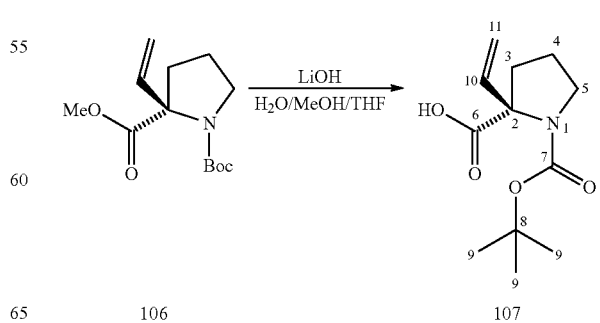

A solution of 858 mg (3.36 mmol, 1.0 eq) of the educt 106 in 3.4 ml (6.72 mmol, 2.0 eq, 2 N) aqueous LiOH solution, 3.4 ml MeOH and 10.2 ml THF (1:1:3) was stirred for 5 h at 50° C. The pH value was checked (pH=10), then the reaction mixture was washed twice with MTBE, and the aqueous phase adjusted to pH=1 at 0° C. by adding 1 N HCl solution. The substance was then extracted 3× with DCM, the combined DCM phases were dried over magnesium sulfate, and the solvent was removed at reduced pressure. The yield was 700 mg (2.90 mmol, 86%) of the product 107 as white solid.

M ($C_{12}H_{19}NO_4$): 241.28 g mol$^{-1}$.
$[\alpha]^{23}_D$: −25.8° (c=0.490, CHCl$_3$).
Melting point: 134.4° C.
$^1$H-NMR (300 MHz, CDCl$_3$): δ=1.34 (Ψ-d, J 29.3(Ψ), 9H, H9), 2.04-1.68 (m, 3H, H4, H3'), 2.42-2.13 (m, 1H, H3), 3.66-3.32 (m, 2H, H5), 5.20-4.87 (m, 2H, H11), 6.29-6.00 (m, 1H, H10), 10.22 (s, 1H, COOH).
$^{13}$C-NMR (75 MHz, CDCl$_3$): δ=21.71/22.56 (t, C4), 27.93/28.19 (q, C9), 37.82/39.16 (t, C3), 47.68/48.26 (t, C5), 69.18/70.15 (s, C2), 80.51/80.81 (s, C8), 113.02/114.02 (t, C11), 136.15/136.48 (d, C10), 153.53/154.84 (s, C7), 175.90/178.08 (s, C6).
IR (FT-ATR): ν=2968 (m, br), 2875 (m), 2620 (w), 1727 (s), 1690 (w), 1634 (s), 1550 (w), 1475 (m), 1449 (m), 1418 (s), 1393 (s), 1366 (s), 1349 (m), 1248 (s), 1214 (w), 1158 (s), 1122 (m), 1078 (m), 1013 (w), 996 (w), 982 (m), 942 (m), 884 (m), 852 (s), 774 (s), 755 (w), 719 (s).
HR-MS: (ESI, $C_{12}H_{19}NNaO_4$): 264.121±0.003 u (264.1212 u).

(S)-di-tert-butyl-pyrrolidin-1,2-dicarboxylate (108)

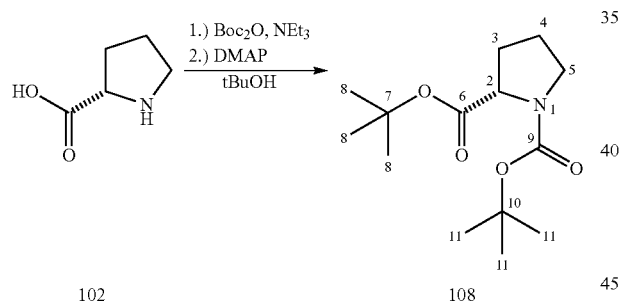

52 ml (251 mmol, 2.7 eq) boc$_2$O was added to 10.1 g (87.73 mmol, 1.0 eq) L-proline (102) in 180 ml tBuOH and 3.70 ml (26.32 mmol, 0.3 eq) NEt$_3$, and the substance was stirred for 4 h at RT until the solution was clear. 3.295 g (26.32 mmol, 0.3 eq) DMAP was then added, and the solution was cooled in an ice bath until showing initial signs of solidifying. The solution was stirred for 17 h at RT and heated over the course of 1.5 h to 45° C., while stifling vigorously, until the formation of gas could no longer be observed. 450 ml MTBE was added to the preparation, the substance was washed in succession with 300 ml each of 1N HCl solution, saturated NaHCO$_3$ solution and saturated NaCl solution, the organic phase was dried over magnesium sulfate, and the solvent was removed at reduced pressure. The yield was 23.8 g (87.70 mmol, 99%) of the protected proline 108 as colorless oil. A small part of the product was purified for analytical purposes by chromatography on silica gel with EtOAc/CyHex (1:9) as eluent.

M ($C_{14}H_{25}NO_4$): 271.35 g mol$^{-1}$.
DC: R$_f$=0.12 (EtOAc/CyHex 1:9).
$[\alpha]^{20}_D$: −53.1° (c (0.670, CHCl$_3$).
$^1$H-NMR (300 MHz, CDCl$_3$): δ=1.51-1.25 (m, 18H, H8, H11), 1.94-1.67 (m, 3H, H4, H3), 2.24-1.94 (m, 1H, H3'), 3.54-3.17 (m, 2H, H5), 4.10 (Ψ-ddd, J 25.5(Ψ), 8.6, 2.9, 1H, H2).
$^{13}$C-NMR (75 MHz, CDCl$_3$): δ=24.05/23.26 (t, C4), 28.21/27.84 (q, C8, C11), 30.74/29.73 (t, C3), 46.35/46.15 (t, C5), 59.52 (d, C2), 79.40/79.20 (s, C10), 80.61 (s, C7), 154.14/153.79 (s, C9), 172.12 (s, C6).
GC-MS: m/z=271 ([M]$^+$, 1), 170 ([M]$^+$-$C_5H_9O_2$, 15), 142 (9), 114 (95), 57 (100), 19 (26).
IR (FT-ATR): ν=2973 (s), 2928 (m), 2880 (w), 1738 (s), 1697 (s), 1476 (m), 1454 (m), 1396 (s), 1364 (s), 1289 (m), 1252 (s), 1215 (s), 1148 (s), 1085 (s), 1028 (w), 978 (m), 939 (m), 917 (m), 895 (m), 851 (m), 840 (m), 797 (w), 770 (m).

(S)-di-tert-butyl-5-methoxypyrrolidine-1,2-dicarboxylate (109)

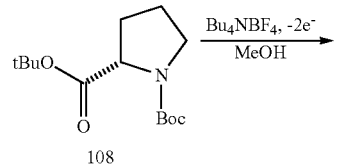

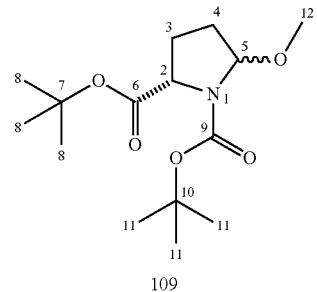

Two graphite plate electrodes (48×56 mm) with a spacing of 5 cm were immersed at 0° C. in a solution of 46.129 g (170.00 mmol) of the protected proline 108 (0.5 M) and 5.6 g (17 mmol) Bu$_4$NBF$_4$ (0.05 M) in 340 ml methanol and electrolyzed at 240 mA constant current strength. The solvent was removed at reduced pressure after the passage of 2.46 F mol$^{-1}$ and filtered with 1000 ml EtOAc/CyHex (1:1) as eluent over silica gel. The solvent was removed at reduced pressure, and 50.624 g (167.97 mmol, 99%) raw product 109 was obtained as clear oil that was reacted further without additional purification. A small part of the product was purified for analytical purposes by means of chromatography on silica gel with EtOAc/CyHex (1:7) as an eluent.

M ($C_{13}H_{27}NO_3$): 301.38 g mol$^{-1}$.
DC: R$_f$=0.43 (EtOAc/CyHex 1:7).
$^1$H-NMR (300 MHz, CDCl$_3$): δ=1.59-1.23 (m, 18H, H8, H11), 2.45-1.62 (m, 4H, H3, H4), 3.63-3.20 (m, 3H, H12), 4.29-3.96 (m, 1H, H2), 5.34-4.99 (m, 1H, H5).
$^{13}$C-NMR (75 MHz, CDCl$_3$: δ=28.23/28.15/27.92/27.82 (C8, C11), 30.82/29.79 (t, C3), 32.89/32.17 (t, C4), 32.89/32.17 (t, C4), 60.24/59.93/59.83/59.62 (d, C2), 80.90/80.69/80.36/80.27 (s, C7, C10), 89.22/88.34 (d, C5), 154.43/154.21/153.81 (s, C9), 171.73/171.67/171.59 (s, C6).
GC-MS: m/z=301 ([M]$^+$, 1), 200 ([M$^{1+}$-$C_5H_9O_2$, 22), 172 (8), 144 (32), 100 (80), 57 (100), 29 (14).

IR (FT-ATR): ν=2975 (s), 2928 (s), 2825 (w), 1738 (s), 1699 (s), 1476 (m), 1455 (m), 1364 (s), 1327 (s), 1252 (s), 1157 (s), 1084 (s), 1024 (m), 987 (s), 939 (s), 911 (s), 885 (s), 841 (s), 797 (s), 772 (s), 729 (m).

(S)-di-tert-butyl-5-cyanopyrrolidine-1,2-dicarboxylate (110)

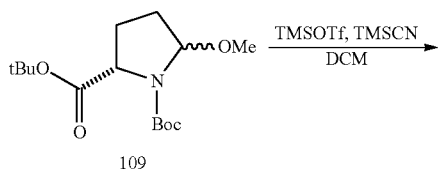

109

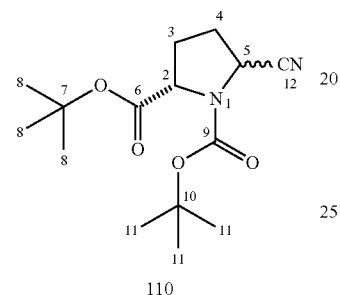

110

4.4 ml TMSOTf (1 vol %) first, then 25.8 ml (191.81 mmol, 1.1 eq) TMSCN were dropped to 50.624 g (167.97 mmol, 1.0 eq) of the raw proline 109 in 440 ml dry DCM at −40° C., then stirred for 1.5 h at this temperature. The solution was admixed with 65 ml MeOH, the solvent removed at reduced pressure and the yield was, obtained by chromatography on neutral aluminum oxide with EtOAc/CyHex 1:9 as eluent, 40.569 g (136.89 mmol, 81% in two steps) of a diastereomer mixture of the nitrile 110 (d.r.: 3:1 cis:trans). A small part of the individual isomers was chromatographically separated for analytical purposes.

M ($C_{15}H_{24}N_2O_4$): 296.36 g mol−1.

trans-DC: $R_f$=0.33 (EtOAc/CyHex 1:9).

trans-$[\alpha]^{20}_D$: −88.6° (c=0.550, CHCl$_3$).

trans-melting point: 106.3° C.

trans-$^1$H-NMR (300 MHz, CDCl$_3$): δ=1.48-1.32 (m, 18H, H8, H11), 2.53-1.97 (m, 4H, H3, H4), 4.20 (Ψ-dd, J 26.2(Ψ), 7.9 1H, H2), 4.61 (Ψ-dd, J 30.2(Ψ), 7.2, 1H, H5).

trans-$^{13}$C-NMR (75 MHz, CDCl$_3$): δ=28.04/27.81 (q, C8, C11), 29.60/28.59/28.46 (t, C3, C4), 47.59/47.48 (d, C5), 59.52/59.41 (d, C2), 81.84/81.78/81.70/81.49 (s, C7, C10), 118.82/118.75 (s, C12), 152.77/152.48 (s, C9), 170.79/170.70 (s, C6).

trans-GC-MS: m/z=255 ([M]$^+$, 1), 199 (5), 154 ([M]$^+$-C$_5$H$_9$O$_2$, 100).

trans-IR (FT-ATR): ν=2973 (m), 2928 (w), 2238 (w), 1734 (s), 1704 (s), 1473 (w), 1455 (m), 1364 (s), 1323 (m), 1306 (m), 1252 (m), 1225 (s), 1144 (s), 1119 (s), 1061 (m), 1034 (w), 987 (w), 914 (m), 842 (m), 820 (w), 773 (m), 756 (w).

trans-HR-MS: (ESI, C$_{15}$H$_{24}$N$_2$NaO$_4$): 319.163±0.001 u (319.1634 u).

cis-DC: $R_f$=0.27 (EtOAc/CyHex 1:9).

cis-$[\alpha]^{20}_D$: 19.2° (c=0.420, CHCl$_3$).

cis-melting point: 81.3° C.

cis-$^1$H-NMR (300 MHz, CDCl$_3$): δ=1.63-1.33 (m, 18H, H8, H10), 2.47-2.00 (m, 4H, H3, H4), 4.16 (Ψ-td, J 14.2(Ψ), 6.7, 6.7, 1H, H2), 4.55 (Ψ-td, J 39.1(Ψ), 5.7, 5.7, 1H, H5).

cis-$^{13}$C-NMR (75 MHz, CDCl$_3$): δ=28.14/27.84 (q, C8, C11), 30.39/29.71/29.64/28.57 (t, C3, C4), 47.52 (d, C5), 60.24/60.19 (d, C2), 82.01/81.91/81.62 (s, C7, C10), 118.38/118.09 (s, C12), 152.50/152.25 (s, C9), 170.53/170.30 (s, C6).

cis-GC-MS: m/z=255 ([M]$^+$, 1), 199 (5), 154 ([M]$^+$-C$_5$H$_9$O$_2$, 100).

cis-IR (FT-ATR): ν=2976 (s), 2982 (m), 2880 (w), 2238 (w), 1738 (s), 1697 (s), 1473 (m), 1455 (m), 1384 (s), 1364 (s), 1286 (s), 1255 (s), 1215 (s), 1150 (s), 1116 (s), 1072 (s), 1028 (m), 986 (m), 950 (m), 935 (m), 905 (m), 878 (m), 842 (s), 769 (s).

cis-HR-MS: (ESI, C$_{15}$H$_{24}$N$_2$NaO$_4$): 319.163±0.001 u (319.1634 u).

(S)-di-tert-butyl-5-formylpyrrolidine-1,2-dicarboxylate (111)

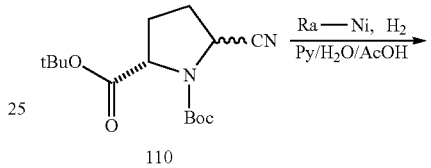

110

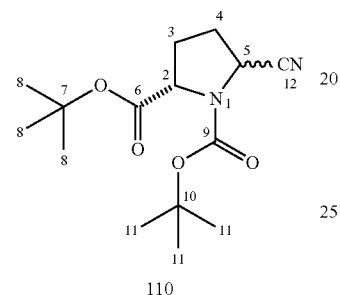

111

90 g Raney-Ni/H$_2$O (50 w % in water, Acros) was added to a solution of 17.905 g (60.42 mmol) of the cyanide 110 in 640 ml Py/AcOH/H$_2$O (2:1:1) and stirred under hydrogen for 72 h at 80° C. 300 ml water was added to the suspension, and the suspension was extracted 3× with 800 ml MTBE each. The combined organic phases were washed twice with water, dried over magnesium sulfate, and the solvent was removed at reduced pressure. The residue was filtered with 1000 ml EtOAc/CyHex (1:1) over silica gel, and, following the removal of the solvent, the raw product was purified by chromatography on silica gel with EtOAc/CyHex 1:4 as eluent. 9.234 g (30.85 mmol, 51%) of the aldehyde 111 was obtained as yellow oil (d.r.: 1.7:1 cis:trans).

M (C$_{15}$H$_{25}$NO$_5$): 299.36 g mol$^{-1}$.

DC: $R_f$=0.27 (EtOAc/CyHex 1:4).

$^1$H-NMR (300 MHz, CDCl$_3$): δ=1.50-1.34 (m, 18H, H8, H11), 2.25-1.83 (m, 4H, H3, H4), 4.53-3.84 (m, 2H, H2, H5), 9.65-9.45 (m, 1H, H12).

$^{13}$C-NMR (75 MHz, CDCl$_3$: δ=29.94/29.20/29.00/28.27/26.29/26.17/25.24/24.56 (t, C3, C4), 28.14/27.90 (q, C8, C11), 60.52/60.38/60.29 (d, C5), 65.28 (d, C2), 81.63/81.54/81.45/81.35/81.23/81.00/80.77 (s, C7, C10), 154.12/153.93/153.55/153.15 (s, C9), 171.54/171.42/171.26 (s, C6), 200.99/200.11 (s, C12).

GC-MS: m/z=299 ([M]$^+$, 1), 270 ([M]$^+$-CO, 5), 198 ([M]$^+$-C$_5$H$_9$O$_2$, 2), 170 (27), 142 (8), 114 (100), 98 (41), 57 (75), 39 (25).

IR (FT-ATR): ν=2976 (s), 2926 (m), 2873 (w), 2806 (w), 2713 (w), 1730 (s), 1695 (s), 1476 (m), 1455 (m), 1383 (s), 1364 (s), 1290 (m), 1253 (s), 1220 (s), 1148 (s), 1123 (s), 1090 (s), 1010 (m), 979 (m), 913 (m), 843 (m), 796 (w), 771 (m).

HR-MS: (ESI, $C_{16}H_{27}NNaO_4$): 320.183±0.001 u (320.1838 u).

(2S,5S)-tert-butyl-5-vinylpyrrolidine-2-carboxylate (113)

(S)-di-tert-butyl-5-vinylpyrrolidine-1,2-dicarboxylate (112)

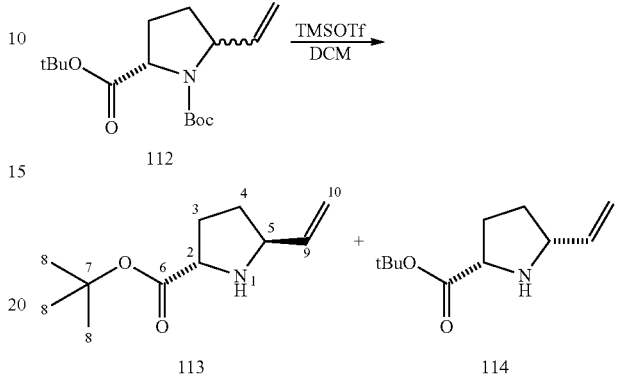

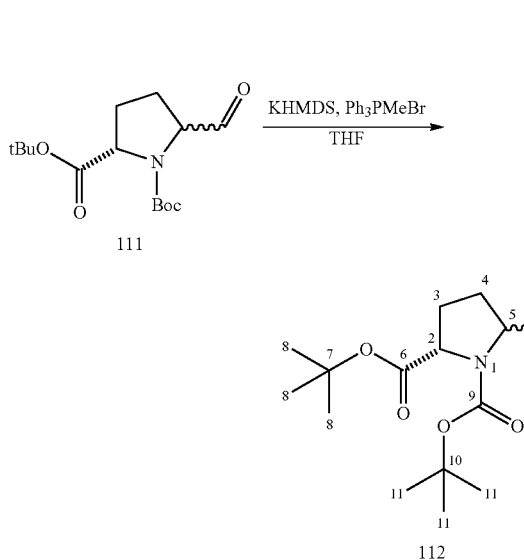

93.5 ml (61.69 mmol, 2.0 eq) of a solution of KHMDS in toluene (15 w %, ABCR) was added under argon at RT to a suspension of 22.037 g (61.69 mmol, 2.0 eq) $Ph_3PMeBr$ in 220 ml THF, and the substance was stirred for 1 h. Then, a solution of 9.234 g (30.88 mmol, 1.0 eq) of the aldehyde 111 in 70 ml THF was dropped in at −78° C., and the resulting solution was stirred for 2.5 h at RT. 160 ml saturated Rochelle salt solution and 100 ml water was added to the reaction mixture, then extracted 3× with 260 ml MTBE each, the combined organic phases were washed with saturated NaCl solution and dried over magnesium sulfate. The solvent was removed at reduced pressure and, after purification by means of column chromatography on silica gel with EtOAc/CyHex (1:9) as eluent, 8.091 g (27.21 mmol, 88%) of the vinyl proline 112 was obtained as an isomeric mixture (d.r.: 1.7:1 cis:trans).

M ($C_{16}H_{27}NO_4$): 297.39 g mol$^{-1}$.
DC: $R_f$=0.27 (EtOAc/CyHex 1:9).
$^1$H-NMR (400 MHz, CDCl$_3$): δ=1.50-1.32 (m, 18H, H8, H11), 2.19-1.59 (m, 4H, H3, H4), 4.58-4.01 (m, 2H, H2, H5), 5.44-4.92 (m, 2H, H13), 5.95-5.60 (m, 1H, H12).
$^{13}$C-NMR (100 MHz, CDCl$_3$): δ=28.32/27.98 (q, C8, C11), 31.54/30.86/29.92/29.00/27.33 (t, C3, C4), 61.00/60.53/60.34/60.17/59.61/59.36 (d, C2, C5), 80.85/79.86/79.78/79.72 (s, C7, C10), 114.93/114.78/114.59/113.82/113.64 (t, C13), 139.21/138.97/138.63/138.50/138.06 (d, C12), 153.73/153.58 (s, C9), 172.09/172.03/171.97 (s, C6).
GC-MS: m/z=297 ([M]$^+$, 1), 196 ([M]$^+$-C$_5$H$_9$O$_2$, 168 (10), 140 (100), 114 (2), 96 (70), 79 (5), 57 (72), 39 (27).
IR (FT-ATR): ν=2975 (s), 2933 (m), 2880 (w), 1737 (s), 1697 (s), 1640 (w), 1477 (m), 1455 (m), 1385 (s), 1363 (s), 1323 (m), 1290 (m), 1255 (m), 1213 (m), 1150 (s), 1106 (s), 1066 (w), 1023 (w), 988 (w), 957 (w), 912 (m), 873 (w), 856 (w), 843 (w), 770 (w).

2.5 ml (13.82 mmol, 1.0 eq) TMSOTf was slowly added to a solution of 4.041 g (13.59 mmol, 1.0 eq) of the vinyl proline 112 in 50 ml DCM under argon at 0° C., the substance was stirred for 5 min, and the reaction was then ended by adding 10 ml saturated NaHCO$_3$ solution. The aqueous phase was extracted 3× with 16 ml DCM each, the combined organic phases were dried over magnesium sulfate, and the solvent was removed at reduced pressure. Following chromatography on silica gel with DCM/MeOH (25:1) as eluent, 887 mg (4.50 mmol, 33%) of the trans-isomer 113 and 1.306 g (6.63 mmol, 49%) of the cis-isomer 114 were obtained.

M ($C_{11}H_{19}NO_2$): 197.27 g mol$^{-1}$.
trans-DC: $R_f$=0.35 (DCM/MeOH 25:1).
trans-$[α]^{20}_D$: −28.9° (c=0.715, CHCl$_3$).
trans-$^1$H-NMR (300 MHz, CDCl$_3$): δ=1.42 (s, 9H, H8), 1.58-1.45 (m, 1H, H4'), 1.96-1.70 (m, 2H, H3, H4), 2.25-2.10 (m, 1H, H3'), 2.70 (s, 1H, NH), 3.77-3.65 (m, 2H, H2, H5), 4.97 (d, J 10.2, 1H, H10), 5.13 (dd, J 17.1, 0.9, 1H, H10'), 5.76 (ddd, J 17.1, 10.1, 7.0, 1H, H9).
trans-$^{13}$C-NMR (75 MHz, CDCl$_3$): δ=28.00 (q, C8), 29.60, 31.79 (t, C3, C4), 59.79, 60.89 (d, C2, C5), 81.01 (s, C7), 114.50 (t, C10), 140.89 (d, C9), 174.90 (s, C6).
trans-GC-MS: m/z=197 ([M]+, 1), 96 ([M]+-C$_5$H9O2, 100), 79 (12), 57 (22), 41 (32), 19 (10).
trans-IR (FT-ATR): ν=3346 (w), 3076 (w), 2974 (s), 2932 (m), 2872 (w), 1723 (s), 1641 (w), 1604 (w), 1591 (w), 1477 (m), 1456 (m) 1391 (s), 1366 (s), 1339 (m), 1226 (s), 1153 (s), 1029 (m), 991 (s), 916 (s), 846 (s), 808 (m), 754 (m) 721 (w), 692 (w), 677 (w).
trans-HR-MS: (ESI, $C_{11}H_{20}NO_2$): 198.149±0.002 u (198.1494 u).
cis-DC: $R_f$=0.27 (DCM/MeOH 25:1).
cis-$[α]^{20}_D$: −25.1° (c=1.475, CHCl$_3$).
cis-$^1$H-NMR (400 MHz, CDCl$_3$): δ=1.44 (s, 9H, H8), 2.28-1.82 (m, 4H, H3, H4), 2.22 (s, 1H, NH), 3.59 (dd, J 14.3, 7.2 1H, H5), 3.67 (dd, J 8.7, 5.2 1H, H2), 5.03 (d, J 10.3, 1H, H10), 5.17 (d, J 17.1, 1H, H10') 5.85 (ddd, J 17.2, 10.2, 7.1, 1H, H9).
cis-$^{13}$C-NMR (100 MHz, CDCl$_3$): δ=28.02 (q, C8), 31.87, 30.37 (t, C3, C4), 60.70 (d, C2), 62.23 (d, C5), 81.13 (s, C7), 115.20 (t, C10), 139.97 (d, C9), 174.33 (s, C6).
cis-GC-MS: m/z=197 ([M]+, 1), 96 ([M]+-C5H9O2, 100), 79 (12), 57 (22), 41 (32), 19 (10).

cis-IR (FT-ATR): ν=3360 (w, br), 2977 (s), 2926 (m), 2873 (w), 1727 (s), 1636 (w), 1473 (w), 1453 (m), 1426 (w), 1390 (m), 1366 (s), 1283 (m), 1246 (s), 1225 (s), 1154 (s), 1100 (m), 1030 (w), 992 (m), 917 (m), 848 (s), 769 (w), 753 (w), 740 (w).

cis-HR-MS: (ESI, $C_{11}H_{20}NO_2$): 198.149±0.001 u (198.1494 u).

(2R)-tert-butyl-2-((5S)-2-(tert-butoxycarbonyl)-5-vinylpyrrolidine-1-carbonyl)-2-vinylpyrrolidine-1-carboxylate (115/116)

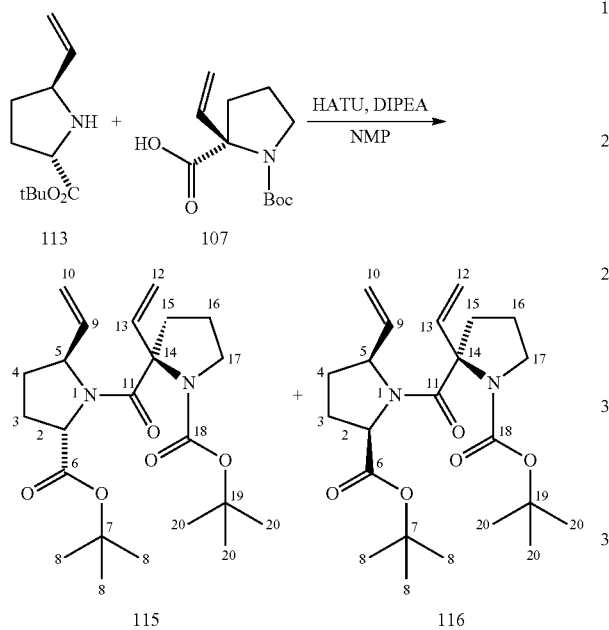

A solution of 743 mg (3.08 mmol, 1.0 eq) of the acid 107, 1.288 g (3.39 mmol, 1.1 eq) HATU and 1.02 ml (6.16 mmol, 2.0 eq) DIPEA in 15 ml NMP was stirred for 20 min at RT. 792 mg (4.02 mmol, 1.3 eq) of the amine 113 was then added, and the solution was heated for 23 h to 85° C. After adding 22 ml 10% aqueous citric acid solution, the substance was extracted 3× with 40 ml MTBE each, the organic phases were washed with 120 ml each of saturated NaHCO$_3$-Lsg., saturated NaCl solution and water, dried over magnesium sulfate, and the solvent was removed at reduced pressure. By chromatography over silica gel with EtOAc/CyHex 1:3 as eluent 539 mg (1.28 mmol, 42%) of a diastereomer mixture (d.r.: 8:1 115:116[)] of the dipeptides 115 and 116 was obtained as yellow oil.

M ($C_{23}H_{36}N_2O_5$): 420.54 g mol$^{-1}$.

DC: $R_f$=0.33 (EtOAc/CyHex 1:3).

$[\alpha]^{20}_D$: −15.6° (c=1.010, CHCl$_3$).

$^1$H-NMR (600 MHz, CDCl$_3$): δ=1.45-1.34 (m, 18H, H8, H20), 1.64-1.57 (m, 1H, H4'), 1.73-1.64 (m, 1H, H3'), 1.85-1.73 (m, 2H, H16), 2.09-2.01 (m, 1H, H3), 2.26-2.13 (m, 2H, H4, H15'), 2.34-2.26 (m, 1H, H15), 3.47-3.36 (m, 1H, H17'), 3.59-3.47 (m, 1H, H17), 4.37-4.26 (m, 0.5H, H2), 4.71 (s, 0.5H, H5), 4.80-4.74 (m, 0.5H, H2), 4.82 (s, 0.5H, H5), 5.10-4.95 (m, 3H, H10', H12), 5.20-5.10 (m, 1H, H10), 5.83-5.63 (m, 1H, H9), 6.69-6.55 (m, 1H, H13).

$^{13}$C-NMR (150 MHz, CDCl$_3$): δ=22.41, 21.63 (t, C16), 25.08, 24.85 (t, C3), 28.27, 27.86 (q, C8, C20), 31.30, 30.69 (t, C4), 36.78, 35.93 (t, C15), 48.31, 48.02 (t, C17), 59.97, 59.69 (d, C5), 61.80, 61.60 (d, C2), 70.71, 70.15 (s, C14), 80.83, 80.66 (s, C7, C19), 112.15 (t, C12), 114.62 (t, C10), 139.75, 138.56 (d, C9), 140.08, 140.02 (d, C13), 154.27, 154.04 (s, C18), 171.40 (s, C11), 171.08 (s, C6).

IR (FT-ATR): ν=3073 (w), 2973 (m), 2926 (w), 2880 (1), 1735 (s), 1693 (s), 1634 (s), 1477 (w), 1455 (w), 1380 (s), 1363 (s), 1300 (w), 1255 (m), 1217 (m), 1149 (s), 1075 (w), 992 (w), 917 (w), 850 (w), 769 (w), 663 (w).

HR-MS: (ESI, $C_{23}H_{36}N_2NaO_5$): 443.253±0.002 u (443.2522 u).

(2'R,3S,8aS)-di-tert-butyl-5-oxo-2,3,5,8a-tetrahydro-1H-spiro[indolizin-6,2' pyrrolidine]-1',3-dicarboxylate (117)

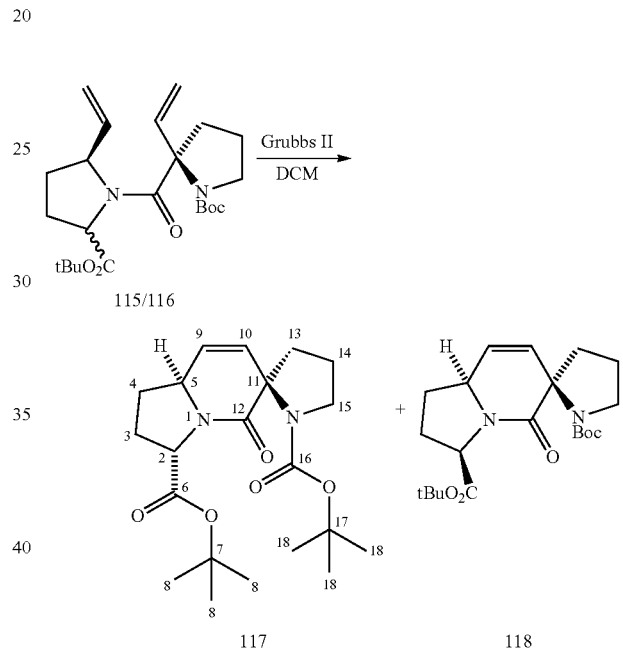

A solution of 135 mg (0.32 mmol, 1.0 eq) of the dipeptides 115 and 116 as well as 82 mg (0.10 mmol, 0.3 eq) Grubbs II in 6.5 ml DCM were heated for 7 h at 55° C. in the microwave (300 W). After adding 0.5 ml DMSO, the substance was stirred overnight at RT, and the solvent was then removed to 100 mbar at reduced pressure. By chromatography on silica gel with EtOAc/CyHex 1:1 as eluent, 65 mg (0.17 mmol, 53%) of the product 117 and 17 mg (0.04 mmol, 13%) of the diastereomer 118 were obtained as gray solid material. In addition, it was possible to re-isolate 30 mg (0.07 mmol, 22%) of the educt 115/116.

M ($C_{21}H_{32}N_2O_5$): 392.49 g mol$^{-1}$.

DC: $R_f$=0.30 (EtOAc/CyHex 1:1).

$[\alpha]^{20}_D$: −138.7° (c=0.265, CHCl$_3$).

Melting point: 128.0° C.

$^1$H-NMR (600 MHz, CDCl$_3$, rotamer mixture; Rot1:Rot2: 1.5:1): rotamer 1: δ=1.30 (s, 9H, H18), 1.44 (s, 9H, H8), 1.56-1.48 (m, 1H, H4'), 1.91-1.75 (m, 3H, H3', H13', H14'), 2.04-1.96 (m, 1H, H14), 2.14-2.10 (m, 1H, H4), 2.27-2.20 (m, 1H, H13), 2.45-2.36 (m, 1H, H3), 3.50-3.41 (m, 1H, H15'), 3.78-3.72 (m, 1H, H15), 4.22-4.16 (m, 1H, H5), 4.46 (t, J 8.8, 1H, H2), 5.72 (dd, J 9.9, 1.4, 1H, H10), 5.79 (dd, J 9.8, 2.8, 1H, H9); rotamer 2: δ=1.40 (s, 9H, H18), 1.43 (s, 9H, H8), 1.75-1.69 (m, 1H, H4'), 1.91-1.75 (m, 3H, H3', H13', H14'), 2.04-1.96 (m, 1H, H14), 2.10-2.05 (m, 1H, H4), 2.27-2.20 (m, 1H, H13), 2.45-2.36 (m, 1H, H3), 3.50-3.41 (m, 1H, H15'), 3.71-3.65 (m, 1H, H15), 4.22-4.16 (m, 1H, H5), 4.56 (t, J 8.6, 1H, H2), 5.80 (dd, J 9.6, 1.4, 1H, H10), 5.88 (dd, J 9.8, 2.7, 1H, H9).

$^{13}$C-NMR (150 MHz, CDCl$_3$, rotamer mixture): δ=22.80, 22.49 (t, C14), 28.21, 28.14 (t, C3), 28.52, 28.32, 27.99 (q, C8, C18), 31.30, 31.14 (t, C4), 39.43, 38.15 (t, C13), 48.26, 47.98 (t, C15), 57.84, 57.62 (d, C2), 58.64, 58.52 (d, C5), 64.28, 64.00 (s, C11), 79.63, 79.39 (s, C17), 81.33, 81.08 (s, C7), 122.46, 121.41 (d, C10), 134.03, 133.37 (d, C9), 154.21, 154.07 (s, C16), 168.05, 167.93 (s, C12), 171.54, 171.25 (s, C6).

IR (FT-ATR): ν=2972 (s), 2929 (m), 2873 (m), 1735 (s), 1696 (s), 1659 (s), 1477 (m), 1432 (s), 1383 (s), 1364 (s), 1293 (m), 1255 (s), 1211 (s), 1149 (s), 1078 (w), 1034 (w), 1004 (m), 959 (w), 928 (w), 884 (w), 870 (w), 843 (w), 803 (w), 786 (w), 770 (w), 734 (w), 702 (w).

Crystal Data 117

| | | |
|---|---|---|
| Identification code | cr297-2 | |
| Empirical formula | C21 H32 N2 O5 | |
| Formula weight | 392.49 | |
| Temperature | 100(2) K | |
| Wavelength | 0.71073 Å | |
| Crystal system, space group | Monoclinic, P21 | |
| Unit cell dimensions | a = 14.4763(17) Å | alpha = 90 deg. |
| | b = 6.8044(4) Å | beta = 102.213(4) deg. |
| | c = 22.803(3) Å | gamma = 90 deg. |
| Volume | 2195.4(4) Å$^3$ | |
| Z, Calculated density | 4, 1.187 Mg/m$^3$ | |
| Absorption coefficient | 0.084 mm$^{-1}$ | |
| F(000) | 848 | |
| Crystal size | .3 × .075 × .05 mm | |
| Theta range for data collection | 2.07 to 27.00 deg. | |
| Limiting indices | −18 ≤ h ≤ 15 −8 ≤ k ≤ 5 | |
| | −29 ≤ l ≤ 21 | |
| Reflections collected/unique | 9852/5126 [R(int) = 0.0693] | |
| Reflection observed [I > 2sigma(I)] | 2646 | |
| Completeness to theta = 27.00 | 98.2% | |
| Absorption correction | None | |
| Refinement method | Full-matrix least-squares on F$^2$ | |
| Data/restraints/parameters | 5126/1/517 | |
| Goodness-of-fit on F$^2$ | 0.828 | |
| Final R indices [I > 2sigma(I)] | R1 = 0.0491, wR2 = 0.0705 | |
| R indices (all data) | R1 = 0.1398, wR2 = 0.0885 | |
| Absolute structure parameter | −0.3(12) | |
| Largest diff. peak and hole | 0.193 and −0.202 e.Å$^{-3}$ | |

Crystal Data 118

| | | |
|---|---|---|
| Identification code | Z2 | |
| Empirical formula | C21 H32 N2 O5 | |
| Formula weight | 392.49 | |
| Temperature | 100(2) K | |
| Wavelength | 0.71073 Å | |
| Crystal system, space group | Monoclinic, P21 | |
| Unit cell dimensions | a = 10.5025(9) Å | alpha = 90 deg. |
| | b = 8.0873(10) Å | beta = 94.484(6) deg. |
| | c = 12.6674(13) Å | gamma = 90 deg. |
| Volume | 1072.6(2) Å$^3$ | |
| Z, Calculated density | 2, 1.215 Mg/m$^3$ | |
| Absorption coefficient | 0.086 mm$^{-1}$ | |
| F(000) | 424 | |
| Crystal size | .2 × .1 × .05 mm | |
| Theta range for data collection | 1.94 to 26.99 deg. | |
| Limiting indices | #NAME? | |
| Reflections collected/unique | 5802/2477 [R(int) = 0.0346] | |
| Reflection observed [I > 2sigma(I)] | 1970 | |
| Completeness to theta = 26.99 | 98.6% | |
| Absorption correction | None | |
| Refinement method | Full-matrix least-squares on F$^2$ | |
| Data/restraints/parameters | 2477/1/259 | |
| Goodness-of-fit on F$^2$ | 1.047 | |
| Final R indices [I > 2sigma(I)] | R1 = 0.0485, wR2 = 0.1243 | |
| R indices (all data) | R1 = 0.0660, wR2 = 0.1334 | |
| Absolute structure parameter | −0.9(15) | |
| Largest diff. peak and hole | 0.649 and −0.294 e.Å$^{-3}$ | |

(2'R,3S,8aS)-1'-(((9H-fluoren-9-yl)methoxy)carbonyl)-5-oxo-2,3,5,8a tetrahydro-1H-spiro[indolizin-6,2'-pyrrolidine]-3-carboxylic acid (85)

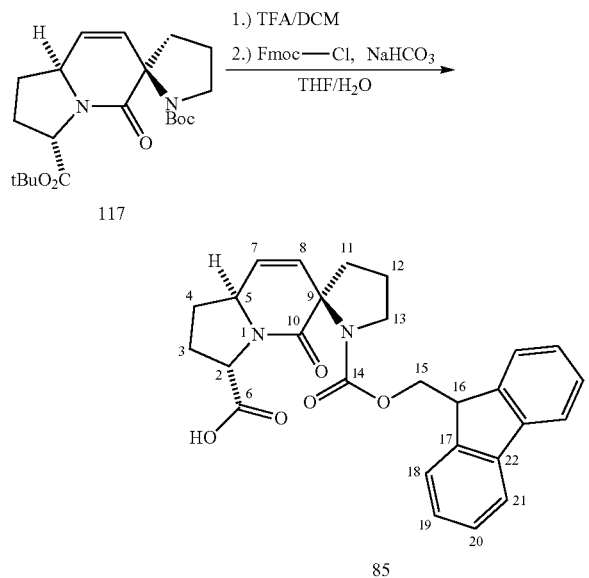

2 ml TFA was added to a solution of 49 mg (0.13 mmol, 1.0 eq) of the dipeptide 117 in 2 ml DCM at 0° C. and then stirred for 1 h at RT. The solvent was removed at reduced pressure, the residue was taken up in 3 ml semi-saturated NaHCO$_3$ solution, and after this the pH value was checked (pH≥8). After this, a solution of 51 mg (0.20 mmol, 1.5 eq) Fmoc-Cl in 1 ml THF was added at 0° C. and stirred overnight at RT. After adding 5 ml DCM, the solution was adjusted at 0° C. with 1 N HCl solution to pH=1. The phases were then separated, and the aqueous phase was extracted twice with DCM. The combined organic phases were dried over magnesium sulfate; the solvent was removed at reduced pressure, and obtained by chromatography on silica gel with DCM/MeOH 15:1 as eluent was as yield 53 mg (0.11 mmol, 85%) of the Fmoc-protected product 85.

M ($C_{27}H_{26}N_2O_5$): 458.51 g mol$^{-1}$.
DC: $R_f$=0.20 (DCM/MeOH 15:1).
Melting point:
$^1$H-NMR (600 MHz, MeOD, rotamer mixture; rot1:rot2 1:1): δ=rotamer 1: δ=1.66-1.55 (m, 1H, H4'), 2.03-1.77 (m, 4H, H3', H11', H12), 2.16-2.08 (m, 1H, H4), 2.34-2.28 (m, 1H, H11), 2.42-2.35 (m, 1H, H3), 3.54-3.45 (m, 1H, H13'), 3.71-3.61 (m, 1H, H13), 4.33-4.16 (m, 3H, H5, H15', H16), 4.41 (t, J 8.7, 1H, H2), 4.54 (dd, J 10.9, 6.0, 1H, H15), 5.69 (dd, J 10.0, 2.4, 1H, H7), 5.87 (dd, J 10.0, 1.1, 1H, H8), 7.32-7.26 (m, 2H, H19), 7.40-7.34 (m, 2H, H20), 7.63-7.50 (m, 2H, H18), 7.79-7.72 (m, 2H, H21); rotamer 2: 1.24-1.15 (m, 1H, H4'), 2.03-1.77 (m, 5H, H3', H4, H11', H12), 2.28-2.23 (m, 1H, H3), 2.34-2.29 (m, 1H, H11), 3.54-3.45 (m, 1H, H13'), 3.71-3.61 (m, 1H, H13), 4.03 (t, J 5.6, 1H, H16), 4.17-4.11 (m, 1H, H5), 4.33-4.17 (m, 3H, H2, H15), 5.48 (dd, J 9.8, 2.6, 1H, H7), 5.58 (d, J 9.9, 1H, H8), 7.32-7.26 (m, 2H, H19), 7.40-7.34 (m, 2H, H20), 7.63-7.50 (m, 2H, H18), 7.79-7.72 (m, 2H, H21).
$^{13}$C-NMR (150 MHz, MeOD, rotamer mixture): δ=24.19/23.25 (t, C12), 29.53/29.45 (t, C3), 32.09/32.05 (t, C4), 40.35/39.46 (t, C11), 48.34 (d, C16), 49.90/49.43 (t, C13), 60.64/60.13 (d, C5), 61.52/61.31 (d, C2), 65.75/65.72 (s, C9), 68.42/67.85 (t, C15), 121.00/120.93 (d, C21), 124.58/124.35 (d, C8), 126.13/126.09/125.97/125.77 (d, C18), 128.12/128.04/127.99 (d, C19), 128.80/128.73 (d, C20), 132.77/131.64 (d, C7), 142.57/142.51 (s, C22), 145.51/145.36, 145.05/145.01 (s, C17), 156.69/155.97 (s, C14), 170.20/170.10 (s, C10), 180.14/179.96 (s, C6).

Abbreviations
abs. absolute
Äq. equivalent(s)
Ar aryl
ATR Attenuated Total Internal Reflectance
9-BBN 9-borabicyclononane
ber. calculated
Bn benzyl
Boc tert-butoxycarbonyl
Boc$_2$O di-tert-butyldicarbonate (Boc anhydride)
CH cyclohexane
Cy cyclohexyl
DC Thin Layer Chromatography, TLC
DCE dichloroethane (1,2-)
DCM dichloromethane
DIBAL-H diisobutylaluminum hydride
DIC diisopropylcarbodiimide
DIP Direct Inlet Probe (mass spectrometry)
DIPEA diisopropylethylamine
DMAP 4-N,N-dimethylaminopyridine
DMF N,N-dimethylformamide
DMP 2,2-dimethoxypropane
DMS dimethylsulfide
DMSO dimethylsulfoxide
dr Diastereomeric Ratio
EE ethylacetate
ee Enantiomeric Excess
EI Electron [Impact] Ionization
ESI Electron Spray Ionization
Et ethyl
Et$_2$O diethylether
EtOH ethanol
EVH1 ENA-VASP-homology 1 domain
FGI Function Group Inversion
Fmoc fluoroenyl-9-methoxycarbonyl
FMP Research Institute for Molecular Pharmacology (Berlin-Buch)
GC-MS Gas Chromatography with connected Mass Spectrometry
gef. found
ges. saturated
HPLC High Performance Liquid Chromatography
HRMS High Resolution Mass Spectrometry
IR Infrared spectroscopy
konz. concentrated
LiHMDS lithium-hexamethyldisilazide
M molar mass
MCPBA meta-chloroperbenzoic acid
Me methyl
MeOH methanol
Ms mesyl (methane sulfonyl)
MS Mass Spectrometry
MTBE methyl-tert-butylether
NaHMDS sodium-hexamethyldisilazide
NME N-methylephedrine
NMR Nuclear Magnetc Resonance spectroscopy
NOE Nuclear Overhauser Effect
ortho
Ph phenyl
PPII polyproline helix type II POM-Cl chloromethyl pivaloate
PPTS pyridinium-para-toluenesulfonate
RCM Ring Closure Metathesis
$R_f$ Retention Factor
[Ru]$_{II}$ Grubbs II catalyst 81
[Ru]$_{gr}$ modified (green) Grubbs Hoveyda catalyst according to Blechert 82
s secondary
Smp. melting point
Su succinimide
TBAF Tetrabutylammonium fluoride
TBS tert-butyldimethylsilyl
t-Bu tert-butyl
Tf Trifluormethansulfonyl
TFA trifluoroascetic acid
THF tetrahydrofuran
TMEDA tetramethylethylenediamine
TMS trimethylsilyl
TMS OTf trimethylsilyl trifluoromethanesulfonate
TPS tert-butyldiphenylsilyl
Ts tosyl (para-toluenesulfonyl)
TsOH para-toluenesulfonic acid
Z benzyloxycarbonyl—(also Cbz)
Single-letter codes and three-letter codes of natural proteinogenic amino acids:

| A | Ala | Alanine | M | Met | Methionine |
|---|-----|---------|---|-----|------------|
| C | Cys | Cysteine | N | Asn | Asparagine |
| D | Asp | Asparaginic acid | P | Pro | Proline |
| E | Glu | Glutaminic acid | Q | Gln | Glutamine |
| F | Phe | Phenylalanine | R | Arg | Arginine |
| G | Gly | Glycine | S | Ser | Serine |
| H | His | Histidine | T | Thr | Threonine |
| I | Ile | Isoleucine | V | Val | Valine |
| K | Lys | Lysine | W | Trp | Tryptophan |
| L | Leu | Leucine | Y | Tyr | Tyrosine |

The invention claimed is:
1. A compound according to general formula 1,

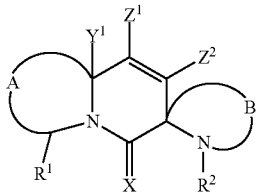

with an unsaturated central ring of six members, wherein
X=0 O or S;
A, B=ring bridges;
Y$^1$=H, alkyl, fluoroalkyl, aryl or heteroaryl;
Z$^1$, Z$^2$=H, carbonyl, OH, O-alkyl, O-acyl or N—R'—R",
with R' and R" being selected from the group consisting of H, alkyl, acyl, sulfonyl, alkyl, acyl,flouralkyl, aryl and heteroaryl;
R$^1$=alkyl, acyl, alkoxycarbonyl, aryloxycarbonyl, aminocarbonyl or CONH-peptidyl; and
R$^2$=H, arkyl, aryl, alkylcarbonyl, arylcarbonyl, alkoxycarbonyl, aminocarbonyl, aryloxycarbonyl, alkylsulfonyl, arylsulfonyl, aminoacyl or peptidyl.

2. The compound according to claim 1, wherein A and B are 5 or 6-atom ring structures, and wherein atoms of the ring structures are selected from the group consisting of C, O, S and N atoms.

3. The compound according to claim 1 according to the general formula 2,

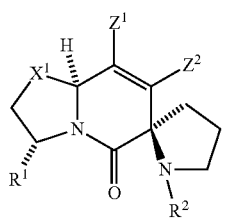

with Z$^1$, Z$^2$ as indicated for formula 1 and the configurations as shown in formula 2,
with R$^1$, R$^2$=alkyl, acyl, heteroaryl or sulfonyl,
with X$^1$=—CH$_2$—, —O— or —S—.

4. The compound according to claim 1, according to formula 3,

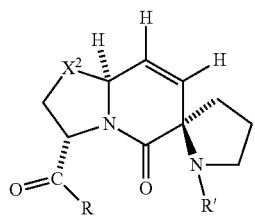

with X$^2$=—CH$_2$—, —O— or —S—,
with R=NH—R", or —O—R", with R"= peptidyl, substituted alkyls or heteroaryl,
with R' = acyl, peptidyl or sulfonyl.

5. A pharmaceutical agent comprising a compound according to claim 1, optionally with a pharmaceutically acceptable carrier substance.

6. The pharmaceutical agent according to claim 5, wherein the pharmaceutically acceptable carrier substance is selected from the group consisting of fillers, extenders, binders, moisteners, dissolution retarders, disintegrators, resorption accelerators, humectants, absorbers and lubricant fillers.

7. A peptide comprising a compound according claim 1.

8. A peptide comprising one or several compounds according to claim 1 and one or several compounds according to structure 86:

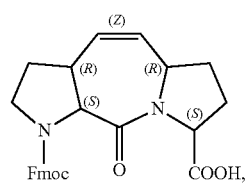

wherein incorporation of the structure 86 into the peptide occurs via one or more bonds between said peptide and structure 86 in place of the Fmoc protection group and/or the COOH group.

9. A peptide selected from the group consisting of:
Ac-(SEQ ID NO: 6)-[2-Cl—F]-p-PP-(SEQ ID NO: 7)—NH$_2$,
Ac-(SEQ ID NO: 6)-[2-Cl—F]-PP-p-(SEQ ID NO: 7)—NH$_2$,
Ac—(SEQ ID NO: 6)-[2-Cl—F]-p-x-(SEQ ID NO: 7)—NH$_2$ and
Ac—(SEQ ID NO: 6)-[2-Cl—F]-p-p-(SEQ ID NO: 7)—NH$_2$,
wherein
p=a compound according to claim 1,
x=structure 86, and
2-Cl—F=2-Cl-phenylalanine, and
wherein incorporation of the structure 86 into the peptide occurs via one or more bonds between said peptide and structure 86 in place of the Fmoc protecting group and/or the COOH group.

10. A peptide according to claim 9, wherein p=structure 85:

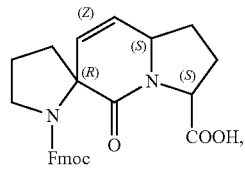

wherein incorporation of the structure 85 into the peptide occurs via one or more bonds between said peptide and structure 85 in place of the Fmoc protecting group and/or the COOH group.

11. A method of modulating a protein comprising: applying a compound according to claim 1 as a ligand to a domain in the protein, wherein the domain is selected from the group consisting of a SRC-homology 3 domain, a WW domain, a ENA-VASP homology 1 domain, a GYF domain, a UEV domain and profiline.

12. The method according to claim 11, wherein the compound is a polyproline mimetic.

13. A method of treating a disease in a subject comprising administering to said subject a compound according to claim 1 to said subject, wherein the disease is is bacterial infectious disease.

14. The method according to claim 13, wherein the bacterial infectious disease is caused by bacteria selected from the group consisting of *Legionella, Streptococci, Staphylococci, Klebsiella, Haemophilis influenzae, Rickettsia, mycobacteria, mycoplasmas, ureaplasmas, Neisseria Pseudomonads, Bordatella, Corynobacteria, Chlamydia, Campylobacter, Escherichia coli, Proteus, Salmonella, Shigella, Yersinia, Vibrio, Enterococci, Clostridia, Borrelia, Triponema pallidum, Brucella, Francisella Leptospira* and *Listeria*.

15. The method according to claim 14, wherein the *Listeria* is selected from the group consisting of *L. monocytogenes* Sv1/2a, *L. monocytogenes* Sv4b F2365, *L. monocytogenes* Sv4b H7858, 178 contigs, *L. monocytogenes* Sv1/2a F6854, 133 contigs, *L. monocytogenes* Sv4b, *L. monocytogenes* Sv4a, *L. innocua* Sv6a, *L. welshimeri* Sv6b, *L. seeligeri* Sv1/2b and *L. ivanovii* Sv5.

\* \* \* \* \*